US010357267B2

(12) United States Patent
Atkins, Jr. et al.

(10) Patent No.: US 10,357,267 B2
(45) Date of Patent: Jul. 23, 2019

(54) SINUS ANESTHESIA KIT

(71) Applicant: ENT Solutions Group LLC, San Antonio, TX (US)

(72) Inventors: James H. Atkins, Jr., San Antonio, TX (US); Lori Rollwitz, San Antonio, TX (US); Raymond L. Weiss, Ocean Springs, MS (US)

(73) Assignee: ENT Solutions Group LLC, San Antonio, TX (US)

( * ) Notice: Subject to any disclaimer, the term of this patent is extended or adjusted under 35 U.S.C. 154(b) by 1158 days.

(21) Appl. No.: 14/446,865

(22) Filed: Jul. 30, 2014

(65) Prior Publication Data

US 2016/0030368 A1    Feb. 4, 2016

(51) Int. Cl.
*A61B 17/24* (2006.01)
*A61K 31/167* (2006.01)
*A61M 31/00* (2006.01)
*A61K 31/137* (2006.01)
*A61K 31/245* (2006.01)
*A61M 5/00* (2006.01)
*A61B 50/00* (2016.01)
*A61B 50/20* (2016.01)
*A61B 50/30* (2016.01)
(Continued)

(52) U.S. Cl.
CPC .............. *A61B 17/24* (2013.01); *A61B 50/00* (2016.02); *A61B 50/20* (2016.02); *A61B 50/30* (2016.02); *A61B 90/92* (2016.02); *A61K 31/00* (2013.01); *A61K 31/137* (2013.01); *A61K 31/167* (2013.01); *A61K 31/245* (2013.01); *A61M 5/002* (2013.01); *A61M 31/00* (2013.01); *A61B 46/00* (2016.02); *A61B 50/33* (2016.02); *A61B 2050/005* (2016.02); *A61B 2050/0059* (2016.02); *A61B 2050/3008* (2016.02); *A61M 2210/0618* (2013.01); *A61M 2210/0681* (2013.01)

(58) Field of Classification Search
CPC .... A61K 9/0043; A61B 17/24; A61M 25/002; A61M 5/002; A61M 2210/0618; A61M 2210/0681
See application file for complete search history.

(56) References Cited

U.S. PATENT DOCUMENTS 6,413,499 B1 * 7/2002 Clay ..................... A61K 9/0043
424/450
6,491,940 B1 * 12/2002 Levin ................... A61K 31/445
424/434
(Continued)

*Primary Examiner* — Nathan R Price
*Assistant Examiner* — Melissa A Snyder
(74) *Attorney, Agent, or Firm* — Campbell Stephenson LLP

(57) ABSTRACT

An apparatus and method for anesthetizing various portions of a patient's nasal sinuses. For example, a kit can be provided that includes a first agent configured to modulate a rate of absorption of a subsequently-applied topical agent by one or more nasal structures. The kit also includes a first applicator configured to apply the first agent to a first portion of the one or more nasal structures. The kit also includes a second agent configured to anesthetize the first portion of the one or more nasal structures subsequent to application of the first agent and a second applicator configured to apply the second agent to the second portion of the one or more nasal structures.

25 Claims, 16 Drawing Sheets

(51) Int. Cl.
*A61B 90/92* (2016.01)
*A61K 31/00* (2006.01)
*A61B 50/33* (2016.01)
*A61B 46/00* (2016.01)

(56) References Cited

U.S. PATENT DOCUMENTS

| | | | |
|---|---|---|---|
| 2005/0245906 A1* | 11/2005 | Makower | A61B 5/06 604/891.1 |
| 2006/0063973 A1* | 3/2006 | Makower | A61B 1/00135 600/114 |
| 2007/0293726 A1* | 12/2007 | Goldfarb | A61B 1/0014 600/178 |
| 2011/0233079 A1* | 9/2011 | Macinnes | A61M 25/002 206/232 |

\* cited by examiner

```
          ┌───────┐
          │ Start │
          └───┬───┘
              │
              ▼
         ╱─────────────╲        710
        ╱  OMU spray    ╲
  No   ╱   effective?    ╲
 ◄────╱                   ╲
      ╲                   ╱
 715   ╲                 ╱
        ╲───────┬───────╱
                │ Yes
   ┌──────────┐ │
   │ Spray OMU│ │
   └────┬─────┘ │
        └───────┤
                ▼
        ┌───────────────┐  720
        │Select implements│
        └───────┬───────┘
                ▼
        ┌───────────────┐  730
        │ Prepare packing│
        └───────┬───────┘
                ▼
        ┌───────────────┐  740
        │ Insert packing │
        └───────┬───────┘
                ▼
        ┌───────────────┐  750
        │Dispose of implements│
        └───────┬───────┘
                ▼
            ┌─────┐
            │ End │
            └─────┘
```

*FIG. 7*

SINUS ANESTHESIA KIT

FIELD OF THE INVENTION

This invention relates to medical instruments, in particular to those used to treat sinus conditions.

DESCRIPTION OF THE RELATED ART

Human sinuses include a group of air filled spaces near the nasal cavity. Various conditions can lead to discomfort or other symptoms associated with the sinuses. One example of such a condition is known as sinusitis, which is an inflammation of the sinuses. Sinusitis can lead to improper drainage of mucous from the sinus cavities. Symptoms of sinusitis include sensations of pain and/or pressure in the head, as well as thick nasal discharge. Sinusitis affects a large number of people. Sometimes sinusitis resolves itself in a matter of days, but in the case of chronic sinusitis, which can persist for months, treatment may be required to relieve the condition.

One treatment for sinus conditions is known as functional endoscopic sinus surgery (FESS). FESS involves surgically removing tissue in an attempt to restore proper drainage of the sinuses. Another treatment is known as balloon sinuplasty. Balloon sinuplasty is less invasive than FESS, since no tissue cutting or removal is involved. However, balloon sinuplasty still involves serious risks of pain and other complications.

BRIEF DESCRIPTION OF THE DRAWINGS

The present invention may be better understood, and its numerous objects, features and advantages made apparent to those skilled in the art by referencing the accompanying drawings.

FIG. 7 is a flow diagram illustrating a method of treating the sinuses, according to one embodiment.

Figure 1:
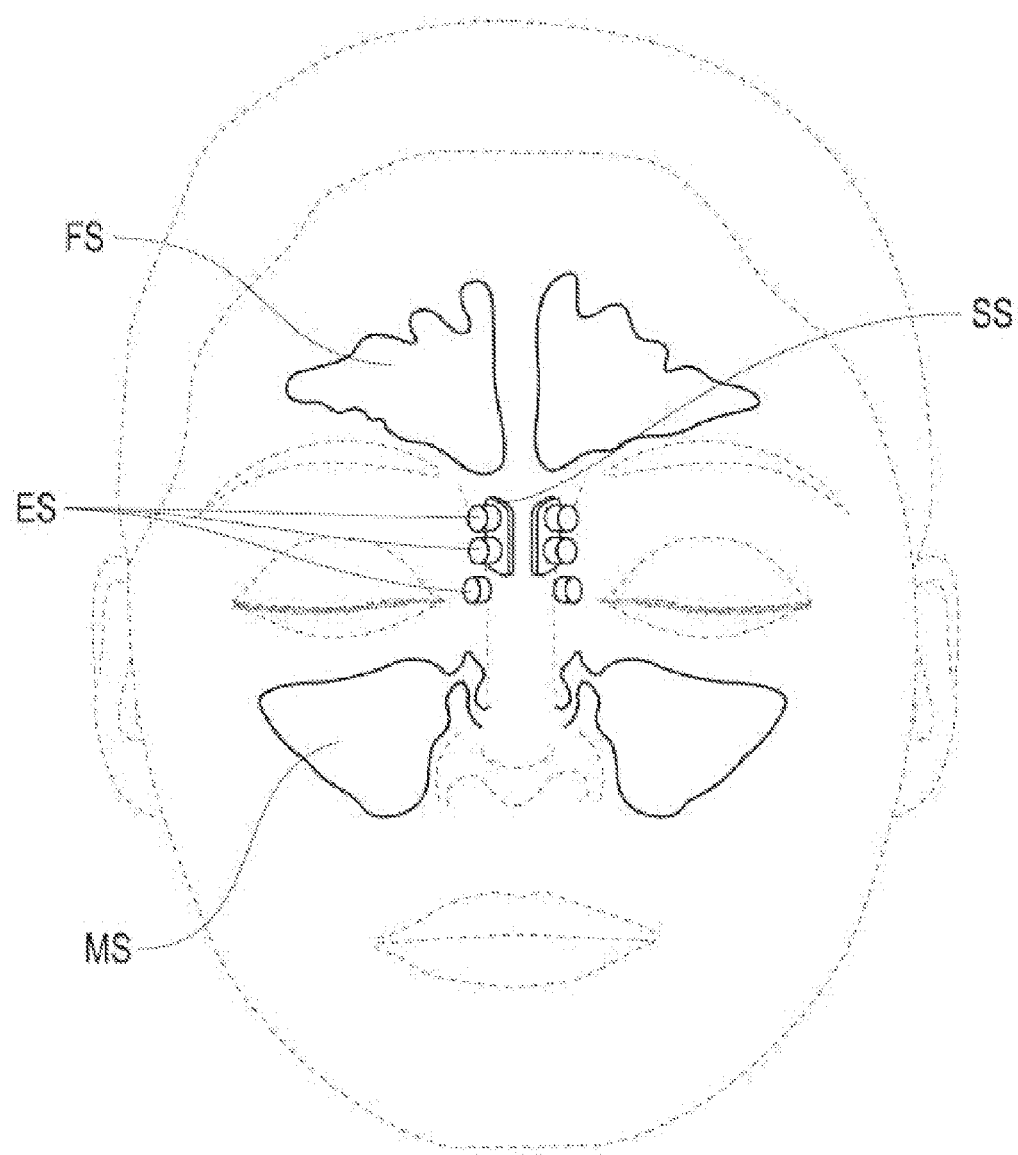
FIG. 1 illustrates the sinuses in relation to the face.

While the invention is susceptible to various modifications and alternative forms, specific embodiments of the invention are provided as examples in the drawings and detailed description. It should be understood that the drawings and detailed description are not intended to limit the invention to the particular form disclosed. Instead, the intention is to cover all modifications, equivalents and alternatives falling within the spirit and scope of the invention as defined by the appended claims.

DETAILED DESCRIPTION

FIG. 1 shows the four paired sinuses, the frontal sinuses (FS), the sphenoid sinuses (SS), the ethmoid sinuses (ES), and the maxillary sinuses (MS). The FS, MS, and SS sinuses produce mucous that drains into the nasal cavity via openings known as ostia. The ES drains into the nasal cavity, though not through distinct ostia. When one or more of the ostia becomes obstructed, either partially or wholly, due to, for example, inflammation of the surrounding tissue, mucous cannot properly drain from the affected sinus and sinusitis symptoms develop.

Figure 2:
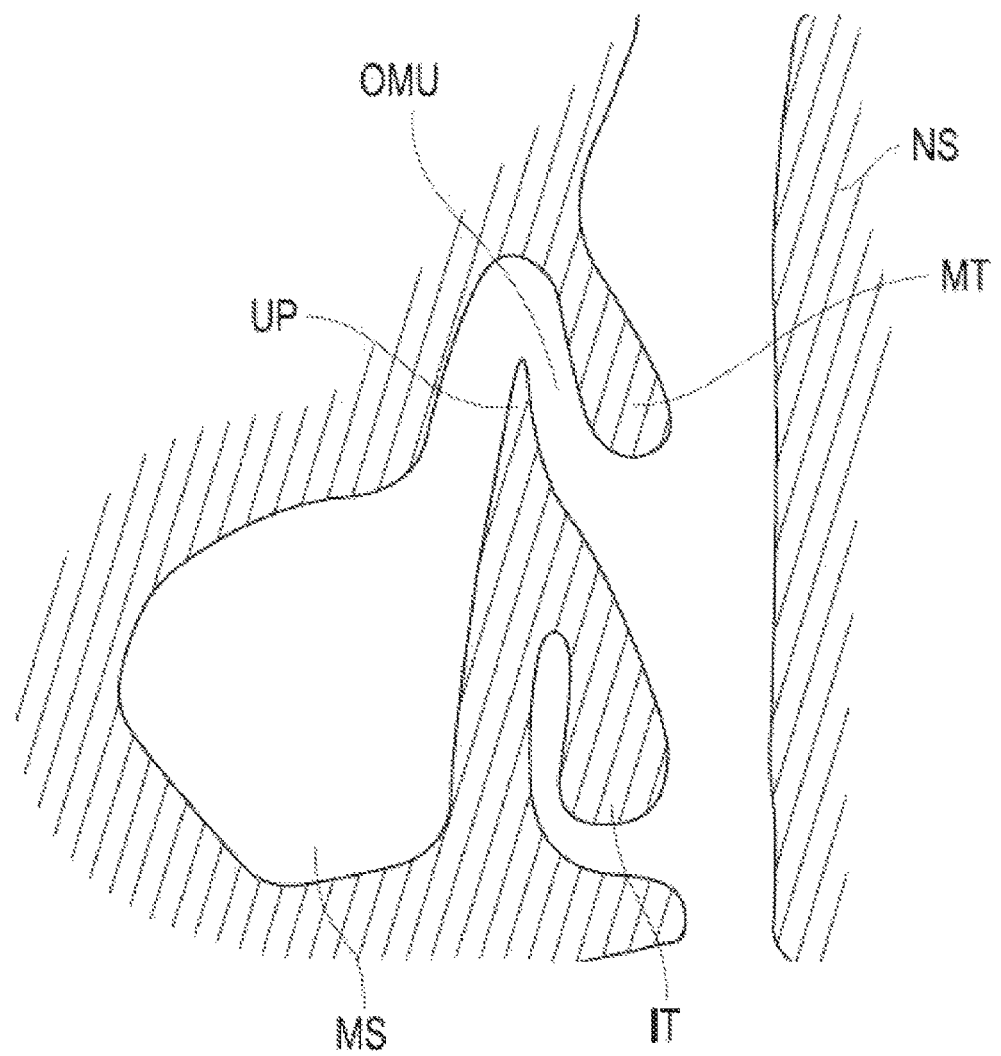
FIG. 2 is a coronal view of a portion of the sinuses.

FIG. 2 is a coronal view of a portion of the sinuses and nasal structures, specifically the maxillary sinus (MS) on a patient's right side. Also shown in FIG. 2 are the uncinate process (UP), the inferior turbinate (IT), the middle turbinate (MT), and the nasal septum (NS), which creates a barrier between the two sides of the nose. The MS drains through the maxillary sinus ostium into the middle meatus. Together the maxillary sinus ostium and the middle meatus are known as the ostiomeatal unit (OMU). The OMU provides an outflow tract for the maxillary sinus.

In order to provide relief from sinusitis and other sinus conditions, various types of sinus procedures can be performed. Sinus procedures are typically performed by an otolaryngologist (ear, nose, and throat (ENT) specialist). Some types of sinus procedures, such as FESS, are typically performed in an operating room (OR) with the patient under general anesthesia. FESS typically involves cutting and removal of tissue which would not be tolerated by patients without general anesthesia in an OR setting. Such procedures typically involve a number of disadvantages, such as a significant degree of pain to the patient, substantial recovery time, relatively high financial cost, need for of numerous medical personnel such as an anesthesiologist and surgical technicians, and logistical complications, such as scheduling an OR.

Other types of procedures can be performed, in some cases, in a physician's office. For example, balloon sinuplasty is performed, in some cases, in the physician's office. In some cases, in-office balloon sinuplasty is not advisable, such as when a patient has one or more of the following conditions: septal deviation obscuring OMU access; massive disease; severe polyposis; allergic fungal sinusitis; need for an image guidance; or phobia of doing the procedure in the office, as examples.

An advantage of balloon sinuplasty is that the procedure can be performed (on at least some patients) using topical and/or topical/local anesthesia, as opposed to general anesthesia. Topical/local anesthesia avoids much of the risk and expense associated with general anesthesia. However, there are still significant risks and complications that can be associated with topical/local anesthesia. Topical/local anesthesia can result in patient discomfort due to the use of needles to deliver anesthetic. Patient discomfort can also result if the patient is insufficiently or improperly anesthetized. Trauma can result from delivery systems, such as needles. Overdose is possible if too much anesthetic is administered due to, for example, accidental administration of too much anesthetic, improper dosage calculations, and/or lack of proper monitoring.

The risks associated with using topical/local anesthesia to perform a sinus procedure are compounded by the fact that significant numbers of medical articles and implements may be involved in performing the sinus procedure. Not only are several different anesthetic agents used in different concentrations, but there are also additional drugs, such as vasoconstrictors, as well as various types of delivery systems, all of which are used in very specific sequence to ensure patient comfort and safety. Preparing these articles and implements before a sinus procedure is an involved task, as is tracking their use during the sinus procedure.

Figure 3:
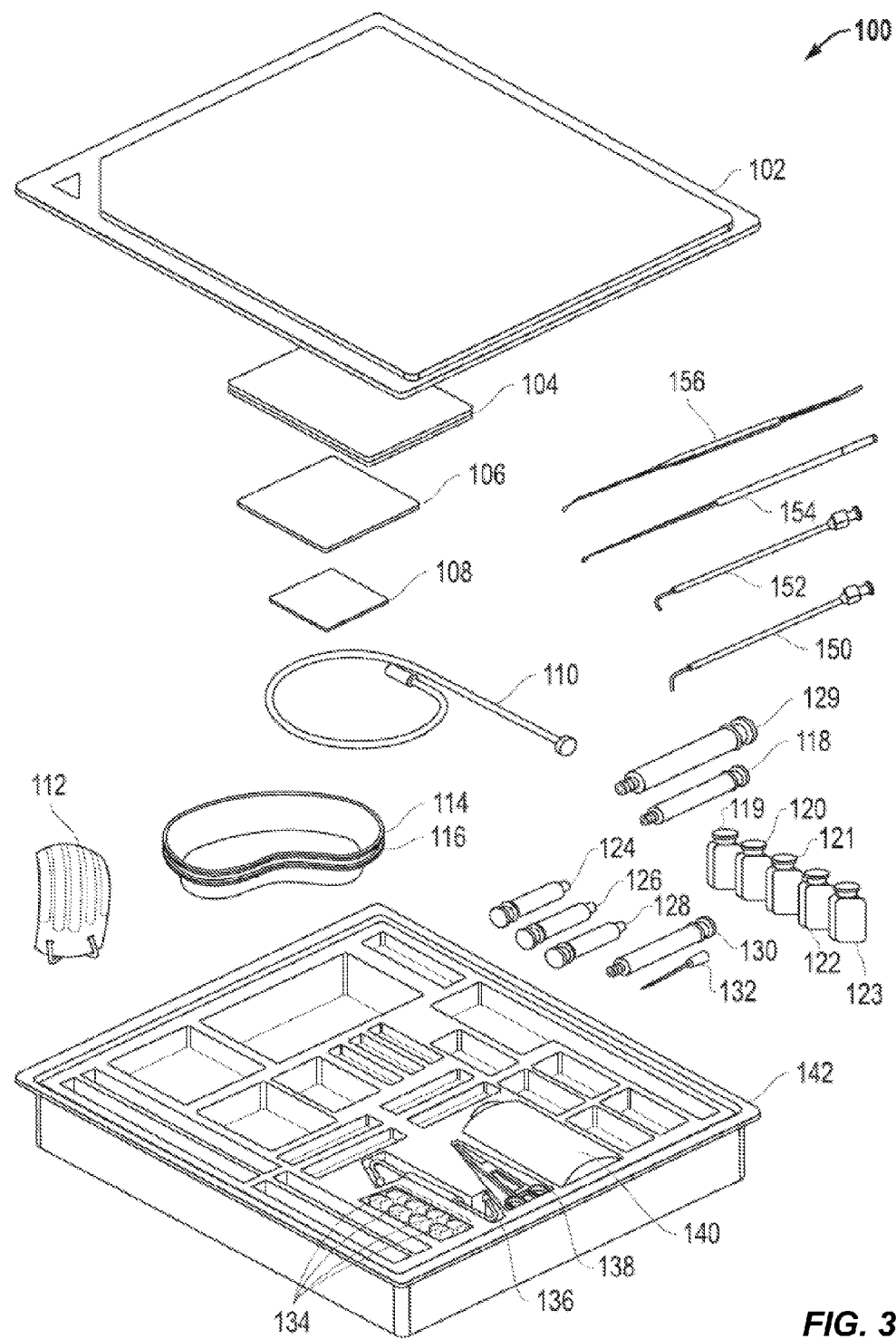
FIG. 3 is a diagram showing a sinus anesthesia kit, according to one embodiment.

FIG. 3 illustrates a kit 100 that includes medical articles and implements configured to be used, for example, to facilitate topical anesthesia of a portion of a patient's paranasal sinuses and nearby nasal structures. The topical anesthesia can be performed in association with performance of a sinus procedure, such as balloon sinuplasty. Kit 100 is configured to enable a physician to achieve safe and effective anesthesia, for example, topical anesthesia of the sinuses, in the physician's office or any other office setting. In one embodiment, safe and effective anesthesia can be achieved without the use of injections, e.g., through topical application of anesthetic and vasoconstrictive agents. It should be understood that kit 100 is not limited to any particular contents or procedure, but is well-suited to achieving safe and effective anesthesia in at least certain procedures.

As shown in FIG. 3, kit 100 includes a tray 142. Tray 142 can be a multi-sided structure constructed of plastic or any other rigid or semi-rigid material. Tray 142 includes recesses for securing objects, such as medical implements used to perform a topical anesthesia procedure. A practitioner can remove and replace the implements in recesses in tray 142. In one embodiment, tray 142 includes information indicating a sequence in which the implements are utilized to effectively perform the procedure. For example, tray 142 can be color coded such that implements placed in recesses which are associated with a certain color are to be used in a specific portion of the procedure. Similarly, alphabetic, numeric, or alphanumeric codes can be used to indicate which part of a procedure given implements are associated with. Kit 100 not only includes the implements used to perform a procedure, but facilitates proper use of the implements, for example by virtue of such information. A removable cover, as shown at 102, is also included to seal kit 100. Removable cover 102, when in place, prevents items included in kit 100 from becoming contaminated or removed. Removable cover 102 can be, for example, plastic, paper, or any other suitable material. Removable cover 102 can be attached to tray 142 using any type of adhesive, heat sealing, or frictional sealing.

In one embodiment, kit 100 includes several pieces 134 of absorbent material. Pieces 134 can be implemented using pieces of cotton, or other such conformable material. Some or all of the pieces can be configured to be more readily retrievable, for example, by virtue of having a string attached to each piece. Pieces 134 can also include information printed or otherwise affixed to facilitate use of each piece in a given procedure. For example, each piece 134 can include information identifying a sequence for insertion or removal or a portion of anatomy corresponding to the piece 134 or other alphabetic, numeric, or alphanumeric identifying information. In one embodiment, pieces 134 are implemented as cottonoids. Pieces 134 can be pre-cut to a specified size calculated to allow pieces 134 to be inserted into and removed from the sinuses and nasal cavity and to contact the nasal structures. Various kits can have different sized pieces 134, for example, smaller pieces 134 for a kit for younger patients. Pieces 134 can be further sized, e.g., cut by medical professionals prior to the procedure. The number of pieces 134 included in kit 100 is predetermined to facilitate safe and effective performance of specified medical procedures.

Pieces 134 are configured to topically deliver substances, such as anesthetics and vasoconstrictors to the sinuses and associated nasal structures by virtue of first absorbing the substances. The amount of such substances allowed to be absorbed into the pieces can be controlled. If an excess is absorbed, some can be removed, e.g., by squeezing the pieces. This not only controls the amount delivered, but prevents other complications from excess amounts, such as fluid running down a patient's throat (a choking, nausea, and discomfort hazard) or impairing visibility and/or accessibility of nasal passages. The amount delivered can also be controlled by a length of time pieces 134 are left in place in the nasal passages. The length of time should be carefully monitored to prevent pieces 134 from drying out and sticking or crusting.

Kit 100 includes one or more tools for insertion and removal of pieces 134. In one embodiment, 0.4 millimeter toothless alligator clips are included, as shown at 138. Kit 100 includes, as shown at 154, an ear curette. Ear curette 154 can be used to effectively position pieces 134 in spaces that are less accessible, e.g., where use of toothless alligator 138 would be impossible or likely to cause patient discomfort.

As shown at 136, kit 100 includes a maxillary seeker. Maxillary seeker 136 can have a first end which is of a particular length and describes a bend of a particular angle and a second end having a different (from the first end) length that describes a bend of a different (from the first end) angle. For example, one end can be bent at 135 degrees and the second end bent at 120 degrees. In one embodiment, maxillary seeker 136 is used to introduce space between a patient's uncinate and lateral nasal wall. Doing so facilitates insertion of a balloon into the sinuses.

Kit 100 includes, as shown at 156, a combination freer elevator and sphenoid seeker. In one embodiment, the sphenoid seeker has a 30 degree bend. The sphenoid seeker can be used to locate the sphenoid opening, e.g., if the sphenoid sinuses are to be anesthetized. The freer elevator can be used to position (medialize and/or lateralize) the middle turbinate. Doing so facilitates access to the OMU.

As shown at 152, kit 100 includes an applicator. In one embodiment, applicator 152 is designed to be used in applying a solid or liquid substance, such as a topical anesthetic gel. Applicator 152 can also be used to move and/or visualize sinus structures. A distal end of applicator 152 can be configured, e.g., bent at an angle, such as 110 degrees, to insert anesthetic gel on, under, and proximate to the uncinate process. A proximal end of applicator 152 can be affixed (e.g., via threads included in the proximal end) to a source of the substance, e.g., a syringe containing anesthetic gel.

Kit 100 includes, as shown at 150, another applicator. In one embodiment, applicator 150 is also designed to be used in applying a solid or liquid substance, such as a topical anesthetic gel. Applicator 150 can also be used to move and/or visualize sinus structures. A distal end of applicator 150 can be configured, e.g., bent at an angle, such as 110 degrees, to insert anesthetic gel into the frontal sinus and face of the sphenoid. A proximal end of applicator 152 can be affixed (e.g., via threads included in the proximal end) to a source of the substance, e.g., a syringe containing anesthetic gel. Applicator 150 is configured to insert the gel into locations which it would be more difficult or impossible to access using applicator 152. Kit 100 may also include one or more implements configured to remove excess anesthetic, not shown, e.g., using suction.

As shown at 110, kit 100 includes a long tipped atomizer, such as a laryngeal madomizer. Laryngeal madomizer 110 can be used to spray an agent, such as an anesthetic and/or vasoconstrictor onto nasal passages. While 110 is shown as a laryngeal madomizer, any other mechanism to introduce a liquid substance can be used. In one embodiment, laryngeal madomizer 110 is long enough that any connections, e.g., to a control syringe at a proximal end, are out of the way when the distal end is introduced into the nose. Laryngeal madomizer 110 is also, in one embodiment, flexible to facilitate ease of use and introduction into the nasal passages. While kit 100 is shown with a single long tipped atomizer, two or more may be included.

Kit 100 includes, as shown at 118, a five cubic centimeter (cc) syringe. In one embodiment, the 5cc syringe can be loaded with an anesthetic and/or vasoconstrictor and coupled to laryngeal madomizer 110 for introduction of the anesthetic and/or vasoconstrictor into the nasal cavity.

As shown at 124, 126, and 128, kit 100 includes three 3cc syringes. In one embodiment, the 3cc syringes can be loaded with an anesthetic and/or a vasoconstrictor and coupled to applicators for the introduction of anesthetic and/or vasoconstrictor into the nasal cavity.

Kit 100 includes, as shown at 129, a 10cc control syringe. In one embodiment, the control syringe can be loaded with sterile saline for irrigation of the nasal cavity. Kit 100 includes, as shown at 140, sterile saline. In one embodiment, kit 100 provides information that enables a physician to easily determine which syringe should be used for a given portion of a procedure. For example, color coding can be used. Tray 142 can include colored markings corresponding to a particular operation or sequence of operations, with different colors corresponding to different operations. Each implement included in kit 100, e.g., syringe, can be located in the tray in a position that identifies the implement as being associated with a particular operation. For example, all implements used in anesthetizing the OMU can be color coded green. The position in the tray can also indicate which portion of the procedure an implement is intended to be used for. For example, implements intended to be used in a given portion can be located near each other. When the procedure calls for anesthetizing the OMU, the practitioner can select only those implements that are identified with the color green. As noted, color coding can be incorporated into tray 142. Color coding can also be incorporated into the implements themselves, e.g., via labels, tinting, or other markings. Color coding is just an example, other information that readily differentiates the implements can be used, such as alphabetic, numeric, or alphanumeric codes. For example, if anesthetizing the OMU is the first step in a procedure, all implements used to anesthetize the OMU can be marked with the number '1'ne, or letter 'A', or some such information. Operations that are performed subsequent (or prior) to anesthetizing the OMU, such as anesthetizing the MT, can be marked with different information to enable the practitioner to readily determine which implements are associated with which portions of the procedure. Such marking helps prevent mistakenly using implements configured to be used for one part of the procedure in another part of the procedure, or failing to use a given implement in the proper manner. This not only improves the convenience, accuracy, and speed with which the practitioner can access the needed implements, but also thereby improves patient safety.

As shown at 130 and 132, respectively, kit 100 includes a syringe and a needle. In one embodiment, needle 132 is a 27 gauge by 1.5 inch needle. Syringe 130 can be loaded with anesthetic and coupled to the needle for introduction of the anesthetic into the nasal structures via the needle.

Kit 100 includes, as shown at 119, a container holding a solution comprised of agents having vasoconstrictive and/or anesthetic properties. For example, the solution can consist of 1% lidocaine mixed with epinephrine. The solution is mixed in a manner known to be safe, stable, and effective for anesthetizing the nasal passages and structures. While lidocaine is given as an example of an anesthetic, any other anesthetic can be used. While epinephrine is given as an example of a vasoconstrictor, any other vasoconstrictor can be used. Container 119 is, in one embodiment, a glass or plastic vial. The amount of solution included in container 119 is predetermined to safely and effectively anesthetize a portion of the sinuses corresponding to a particular operation of the procedure. Kit 100 also includes information identifying which portion of the procedure container 119 is to be used in. The information can include markings on tray 142 and/or on container 119. For example, container 119 and/or tray 142 can be color-coded and/or can include alphabetic, numeric, and/or alphanumeric coding such that the purpose container 119 is intended for is readily apparent from a visual inspection of the kit. Having a pre-mixed and premeasured solution reduces the likelihood of mistakenly applying the wrong agent or the wrong amount of a given agent. The marking information further reduces the likelihood of mistakenly applying the wrong agent or the wrong amount of a given agent.

As shown at 120, kit 100 includes a container including a vasoconstrictive agent. In one embodiment, the vasoconstrictive agent is epinephrine in a concentration of one part per thousand. While epinephrine is given as an example of a vasoconstrictor, any other vasoconstrictor can be used. Container 120 is, in one embodiment, a glass or plastic vial. The amount of vasoconstrictive agent included in container 120 is predetermined to safely and effectively vasoconstrict a portion of the sinuses corresponding to a particular operation of the procedure.

As shown at 121, kit 100 includes a container including an anesthetic agent. In one embodiment, the ansesthetic agent is tetracaine. While tetracaine is given as an example of an anesthetic agent, any other anesthetic agent can be used. Container 121 is, in one embodiment, a glass or plastic vial. The amount of anesthetic agent included in container 121 is predetermined to safely and effectively anesthetize a portion of the sinuses corresponding to a particular operation of the procedure.

Kit 100 includes, as shown at 122, a container including an anesthetic agent. In one embodiment, container 122 contains tetracaine gel. While tetracaine gel is given as an example of an anesthetic agent, any other anesthetic agent can be used. Container 122 is, in one embodiment, a glass or plastic vial. The amount of anesthetic agent included in container 122 is predetermined to safely and effectively anesthetize a portion of the sinuses corresponding to a particular operation of the procedure.

As shown at 123, kit 100 includes a container having a solution comprised of agents having vasoconstrictive and/or anesthetic properties. For example, the solution can consist of a mixture of afrin and tetracaine, e.g., in a 50/50 ratio.

While tetracaine is given as an example of an anesthetic, any other anesthetic can be used. While afrin is given as an example of a vasoconstrictor, any other vasoconstrictor can be used.

In one embodiment, for each of the containers 120-123, kit 100 also includes information identifying which portion of the procedure the respective containers are to be used in. The information can include markings on tray 142 and/or on the respective containers and/or position in tray 142. For example, one of containers 120-123 and/or tray 142 can be color-coded and/or can include alphabetic, numeric, and/or alphanumeric coding such that the purpose each respective is intended for is readily apparent from a visual inspection of the kit. Having pre-mixed and pre-measured anesthetic and vasoconstrictive agents reduces the likelihood of mistakenly applying the wrong agent or the wrong amount of a given agent. The marking information further reduces the likelihood of mistakenly applying the wrong agent or the wrong amount of a given agent.

As shown at 114 and 116, kit 100 includes one or more emesis basins. Emesis basins 114 and 116 can be color coded to be used in different tasks, such as preparation of anesthetics and collection and disposal of used implements.

Kit 100 includes, as shown at 104, one or more sterile gauze pads, for example four inch by four inch pads. Also included in kit 100, as shown at 106, is a non-fenestrated drape or towel. As shown at 108, kit 100 includes a fog reduction/elimination device (FRED). Kit 100 includes, as shown at 112, a nasal drip pad which is provided to the patient after the procedure.

While FIG. 3 describes various implements included in a kit configured to enable safe and effective surgical procedures, kit 100 is not limited to the implements shown. Fewer or additional implements can be included in kit 100.

Figure 4:
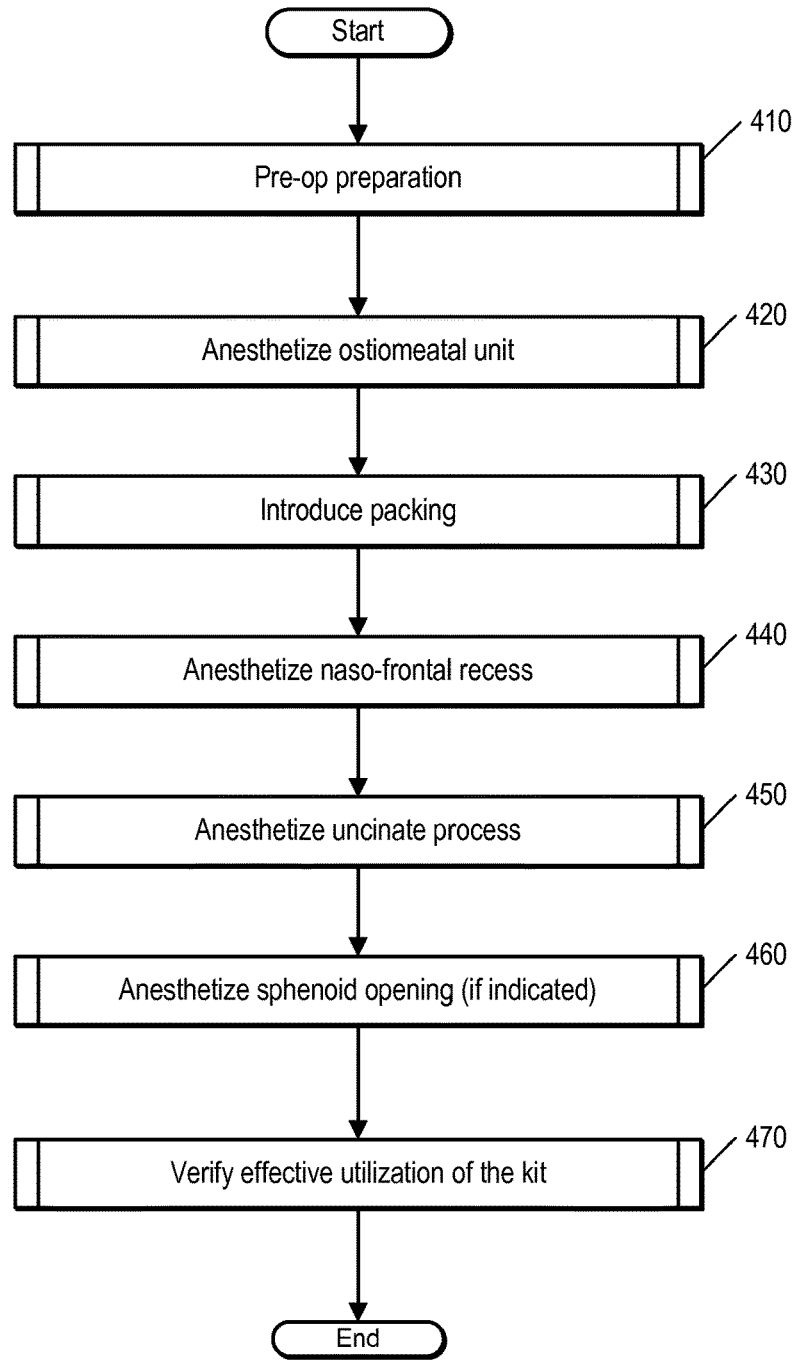
FIG. 4 is a flow diagram illustrating a method of treating the sinuses, according to one embodiment.

FIG. 4 is a flow diagram illustrating a method of treating the sinuses. In one embodiment, performing the method illustrated provides safe and effective anesthesia of a patient's nasal passages and structures such that an in-office procedure, such as balloon sinuplasty can be performed. The method illustrated in FIG. 4 can be performed by one or more medical personnel, such as physicians, physician's assistants, medical assistants, nurses, and the like, referred to herein as practitioners.

Figure 5:
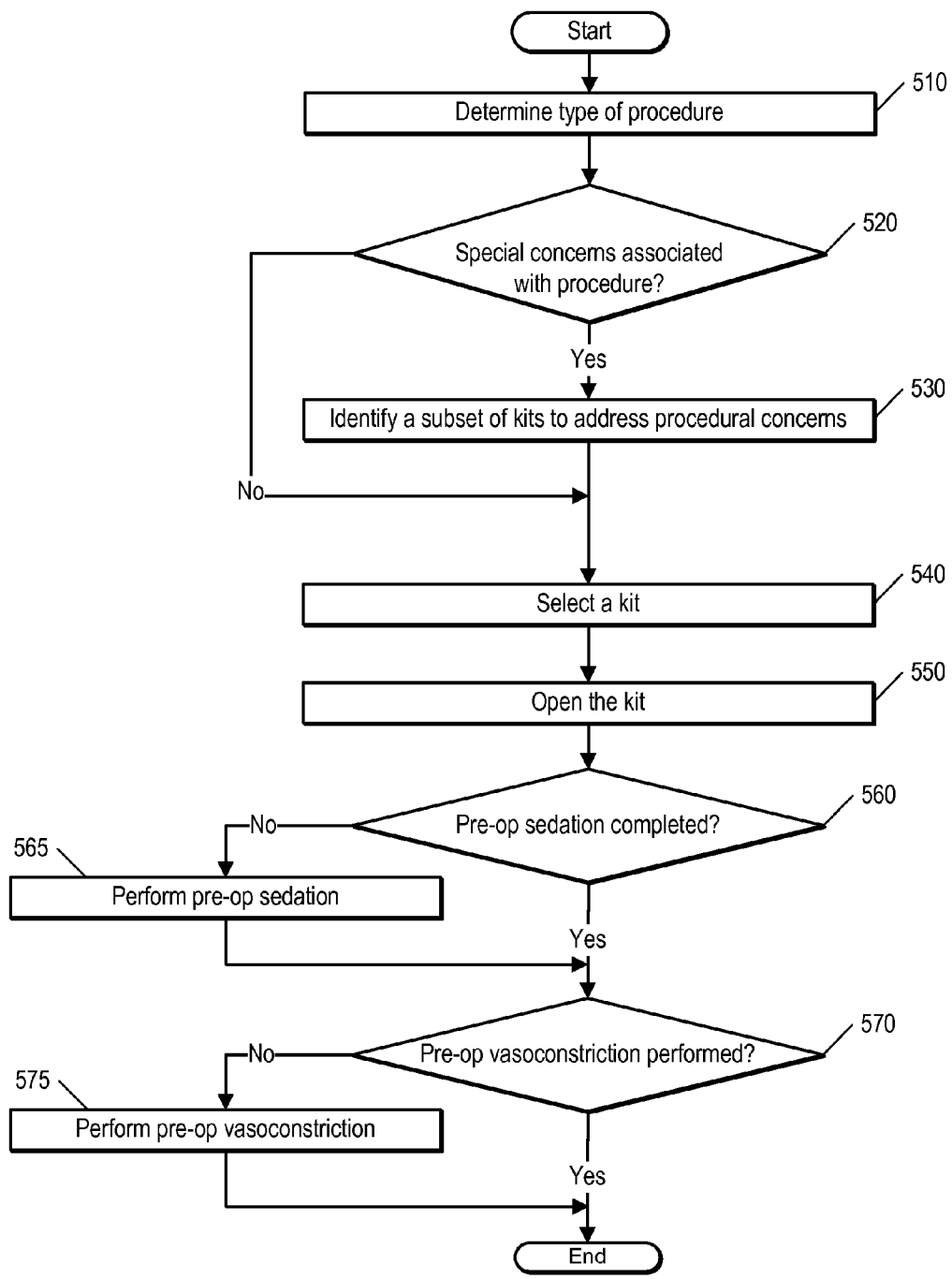
FIG. 5 is a flow diagram illustrating a method of treating the sinuses, according to one embodiment.

At 410, the practitioner performs pre-operative preparation, as discussed in greater detail with regard to FIG. 5. One aspect of pre-operative preparation involves ensuring that a kit, such as kit 100 of FIG. 1, is selected to achieve safe and effective sinus anesthesia. After pre-operative preparation is performed, the practitioner, at 420, anesthetizes the OMU. Additional details of anesthetizing the OMU are discussed with regard to FIGS. 6 and 6A. The practitioner selects and utilizes one or more implements from the kit, as indicated by the kit, to perform 420.

Anesthetizing the OMU facilitates additional access to the OMU, as well as access to additional portions of the sinuses, such as the nasofrontal recess, the MT, and the UP. Such access is facilitated by virtue of the patient being anesthetized such that that the nasal structures are not too sensitive for subsequent portions of the procedure. The practitioner can introduce, at 430, packing into the OMU. Such packing can be saturated or partially saturated with anesthetic and/or vasoconstrictive agents. Both the packing and the agents are included in the kit. Additional details of introducing the packing are discussed with regard to FIGS. 7 and 7A.

As shown at 440, the practitioner next anesthetizes the nasofrontal recess. Additional details of anesthetizing the nasofrontal recess are discussed with regard to FIGS. 8 and 8A. The practitioner anesthetizes, as shown at 450, the UP. Additional details of anesthetizing the UP are discussed with regard to FIGS. 9 and 9A. Depending on the type of procedure that is to be performed, the practitioner may anesthetize the sphenoid opening, as shown at 460. Additional details of anesthetizing the sphenoid opening are discussed with regard to FIGS. 10 and 10A.

After the various parts of the sinuses have been anesthetized, the practitioner verifies, at 470, that the anesthesia procedure was safe and effective. Additional details of verifying safety and efficacy are discussed with regard to FIG. 11. In one embodiment, additional anesthetic is applied at 470.

FIG. 5 shows additional details of a method of performing pre-operative preparation. FIG. 5 can be performed by a practitioner using a kit, such as kit 100 of FIG. 3. At 510, the practitioner determines the type of procedure that will be performed on a patient. In one embodiment, an in-office balloon sinuplasty procedure will be performed and the kit is used to perform needle-free anesthesia prior to the balloon sinuplasty. Whether the balloon sinuplasty will target the maxillary sinuses, frontal sinuses, or sphenoid sinuses, or a combination of those sinuses depends, for example, on the severity of the sinus condition being treated. At 510, the practitioner determines, e.g., using the patient's medical chart, which sinuses are being treated.

At 520, the practitioner determines whether there are any special concerns with the procedure. For example, the practitioner can confirm whether the patient has any allergies or conditions which suggest alternative or atypical medicines or implements. The practitioner can also confirm that there are no special size considerations or structural anomalies in the patient.

If, as determined at 520, there are special considerations, the practitioner identifies a subset of available kits which is configured to address the special considerations. For example, if a patient has a drug allergy, or is unusually small, the practitioner can identify kits that includes a non-allergen drug, or smaller implements. Such identification can be made in advance of the scheduled procedure, or can be made when the patient arrives, using an inventory of available kits.

The practitioner selects, at 540, a kit to be used in anesthetizing the patient. The selection can be based on special considerations, procedure type, and the like. At 550, the practitioner opens the kit. In one embodiment, the practitioner confirms, e.g., using an included checklist, that the kit includes all proper components.

At 560, the practitioner determines whether pre-operative sedation was performed and is effective. In one embodiment, the patient is instructed to take sedation (e.g., lortab and/or valium, or similar sedative/pain medication combinations), as well as to eat a healthy meal with lots of liquids, prior to having the procedure illustrated in FIG. 4 performed. The sedation can help with any phobia or anxiety and the meal helps reduce the chance of a vasovagal response from the patient. If the patient has not been properly sedated, the practitioner administers instructions and/or sedation to the patient, at 565.

The practitioner determines, at 570, whether pre-operative vasoconstriction has been performed. In one embodiment, a patient is instructed to apply a vasoconstrictor, such as oxymetazoline, to the nasal passages one to two hours before arriving at the practitioner's office. If the practitioner determines that pre-operative vasoconstriction was not performed, or is ineffective, the practitioner administers instructions and/or a vasoconstrictor to the patient. After the pre-operative preparation has been completed, the practitioner proceeds with the procedure.

Figure 6:
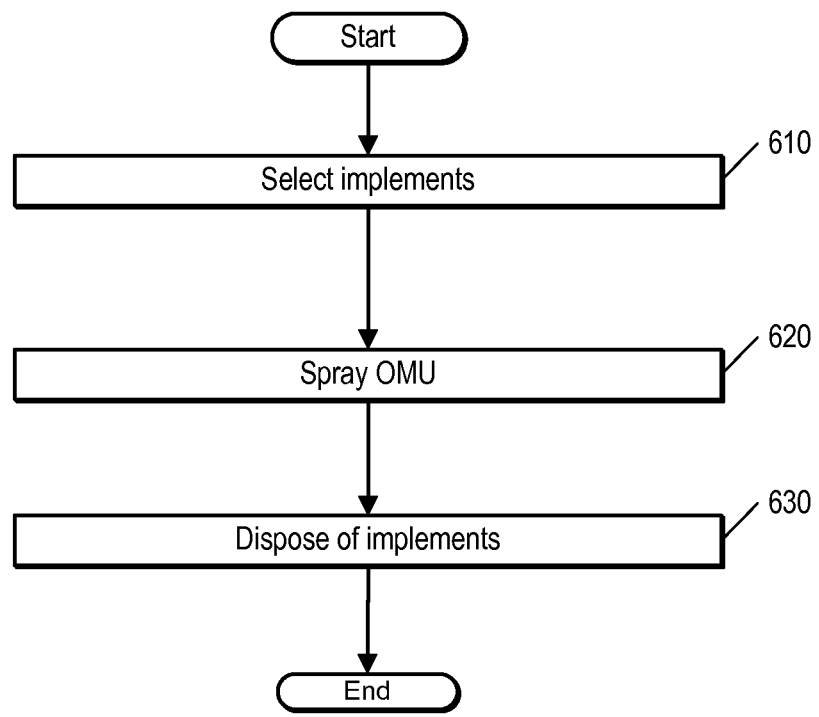
FIG. 6 is a flow diagram illustrating a method of treating the sinuses, according to one embodiment.

FIG. 6 is a flow diagram illustrating a method of treating the sinuses, according to one embodiment. Specifically, FIG. 6 illustrates elements of a procedure for anesthetizing a patient's OMU prior to performing an in-office sinus procedure, such as balloon sinuplasty. FIG. 6 illustrates additional details of 420 of FIG. 4. FIG. 6 can be performed by a practitioner using a kit, such as kit 100 of FIG. 3.

The practitioner selects, at 610, one or more implements used to anesthetize the OMU. In one embodiment, all implements used for anesthetizing the OMU are marked for identification as being associated with this portion of the procedure. For example, implements configured to successfully mate to safely and effectively deliver an agent to the OMU, as well as the agent or agents can all be marked with information to indicate intended use for anesthetizing the OMU. In one embodiment, the practitioner retrieves a laryngeal madomizer (such as shown at 110 of FIG. 3) from the kit. The practitioner loads a solution of 1% lidocaine mixed with epinephrine (e.g., from 119 of FIG. 3) into a 5cc syringe (such as 124 of FIG. 3). The practitioner affixes the laryngeal madomizer to the syringe.

Figure 6A:
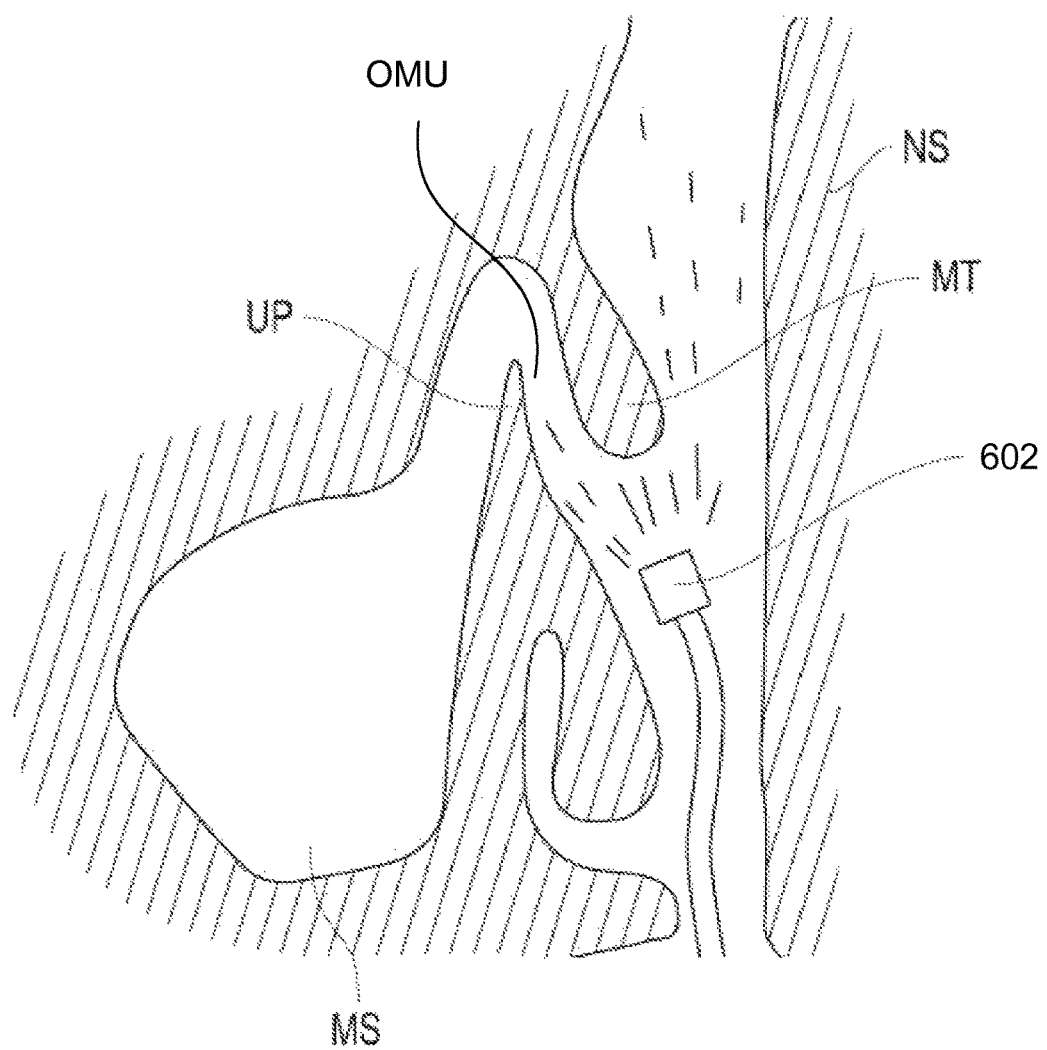
FIG. 6A is a coronal view of a portion of the sinuses being treated, according to one embodiment.

At 620, the practitioner sprays the patient's OMU with an anesthetic agent. In one embodiment, the practitioner depresses the plunger on the syringe to cause the anesthetic to be sprayed onto the nasal structures including the OMU. FIG. 6A illustrates the OMU being sprayed. After spraying the OMU and nearby structures, the practitioner waits for the anesthetic to be absorbed into the OMU and nearby structures and become effective. In one embodiment, practitioner physician waits approximately five to seven minutes. This anesthesia enables the practitioner to perform subsequent steps, e.g., anesthetize additional structures that are higher in the nasal cavity. The practitioner would otherwise be unable to perform the subsequent steps, for example due to patient discomfort.

The practitioner disposes, at 630, the implements used to anesthetize the OMU. In one embodiment, disposing of the implements involves returning the implements to the locations in the kit from which the implements were previously removed. Alternatively, the implements can be placed in a waste receptacle, which can be included in the kit. Disposing of the implements in an ordered fashion enhances accountability and reduces the possibilities of a mistaken use of one or more of the implements included in the kit.

FIG. 6A is a coronal view of a portion of the sinuses being treated, according to one embodiment. FIG. 6A illustrates a distal end 602 of a laryngeal madomizer inserted into a patient's nasal cavity. Distal end 602 is shown spraying an anesthetic agent onto a patient's OMU and nearby nasal structures. The proximal end of the laryngeal madomizer is mated to a source for the anesthetic agent, such as a syringe.

FIG. 7 is a flow diagram illustrating a method of treating the sinuses, according to one embodiment. Specifically, FIG. 7 illustrates elements of a procedure for providing additional anesthesia to a patient's OMU prior to performing an in-office sinus procedure, such as balloon sinuplasty. FIG. 7 can be performed by a practitioner using a kit, such as kit 100 of FIG. 3.

At 710, the practitioner confirms whether the OMU spray has achieved effective anesthesia. In one embodiment, the practitioner probes the area and questions the patient. If the patient discomfort is higher than expected, the practitioner sprays the OMU with additional anesthetic at 715.

The practitioner selects, at 720, implements used to further anesthetize the OMU by introducing packing into the OMU. In one embodiment, all implements used for packing the OMU are marked for identification as being associated with this portion of the procedure. In one embodiment, the practitioner selects an emesis basin, such as 114 or 116 of FIG. 3. The practitioner also retrieves several cotton pieces and/or cottonoids, such as 134 of FIG. 3. The practitioner also retrieves a mixture of anesthetic and vasoconstrictor. In one embodiment, the mixture is a combination of a 4% tetracaine solution with epinephrine in a 1:3000) concentration. The mixture can be pre-mixed or can be mixed at the time of selection. Pre-mixing promotes use of a safe and effective concentration. To introduce the packing into the nose, the practitioner selects one or more implements, such as an ear curette (e.g., 154 of FIG. 3) and/or a toothless alligator (e.g., 138 of FIG. 3).

At 730, the practitioner prepares the packing. In one embodiment, this involves the practitioner placing the packing into the emesis basin and soaking the packing with the mixture. Once the packing is saturated, or the desired amount of the mixture is absorbed, the practitioner can compress the packing to remove excess fluid.

The practitioner introduces the packing into the OMU at 740. The packing is inserted using toothless alligators and/or an ear curette. The shape and conformability of the packing ensure that the entire surfaces of the MT and nearby structures are safely and effectively anesthetized. Using conformable structures containing anesthetic and/or vasoconstrictive agents, the practitioner anesthetizes further into the nasal passages, allowing performance of subsequent steps. Additional details regarding the anesthetic packing are discussed with regard to FIG. 7A. The packing is left in place for a period of time, such as ten minutes. Then the physician removes the packing. The MT should appear visibly vasoconstricted. The anesthetizing of the MT enables the physician to medialize the MT without causing the patient pain. Medializing the MT affords the physician improved access to the OMU, both with instruments and visually.

The practitioner disposes, at 750, of the implements used to pack OMU. In one embodiment, disposing of the implements involves returning the implements to the locations in the kit from which the implements were previously removed. Alternatively, the implements can be placed in a waste receptacle, which can be included in the kit.

Figure 7A:
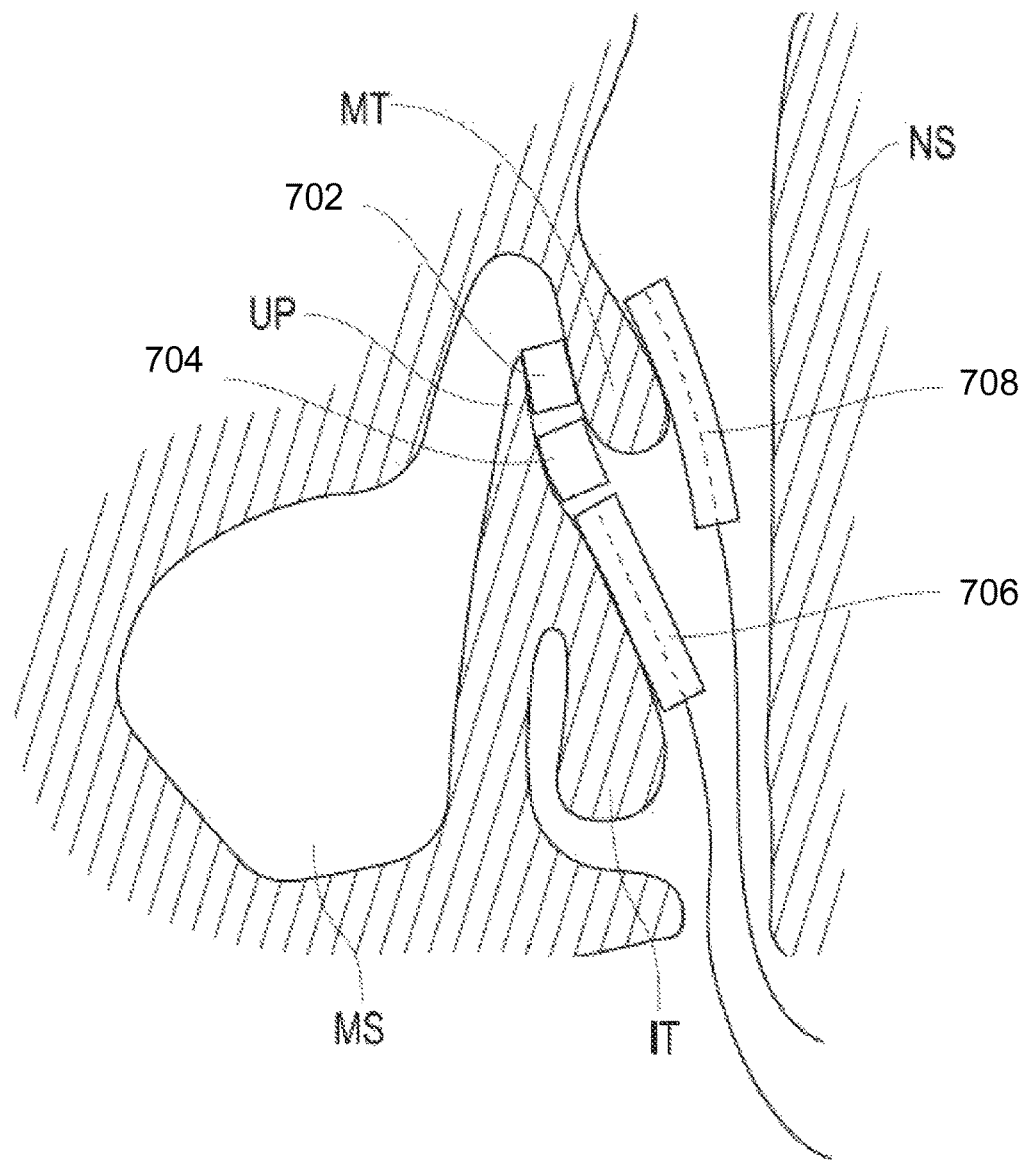
FIG. 7A is a coronal view of a portion of the sinuses being treated, according to one embodiment.

FIG. 7A is a coronal view of a portion of the sinuses being treated, according to one embodiment. FIG. 7A shows the nasal passages packed with absorbent material which has been soaked in a mixture of anesthetic and vasoconstrictor.

In one embodiment, cotton pieces 702 and 704 are used for the middle meatus and cottonoids 706 and 708 are used for the nearby passages. The cottonoids provide improved capacity for retrieval in spaces where the cottonoids could become dislodged.

Figure 8:
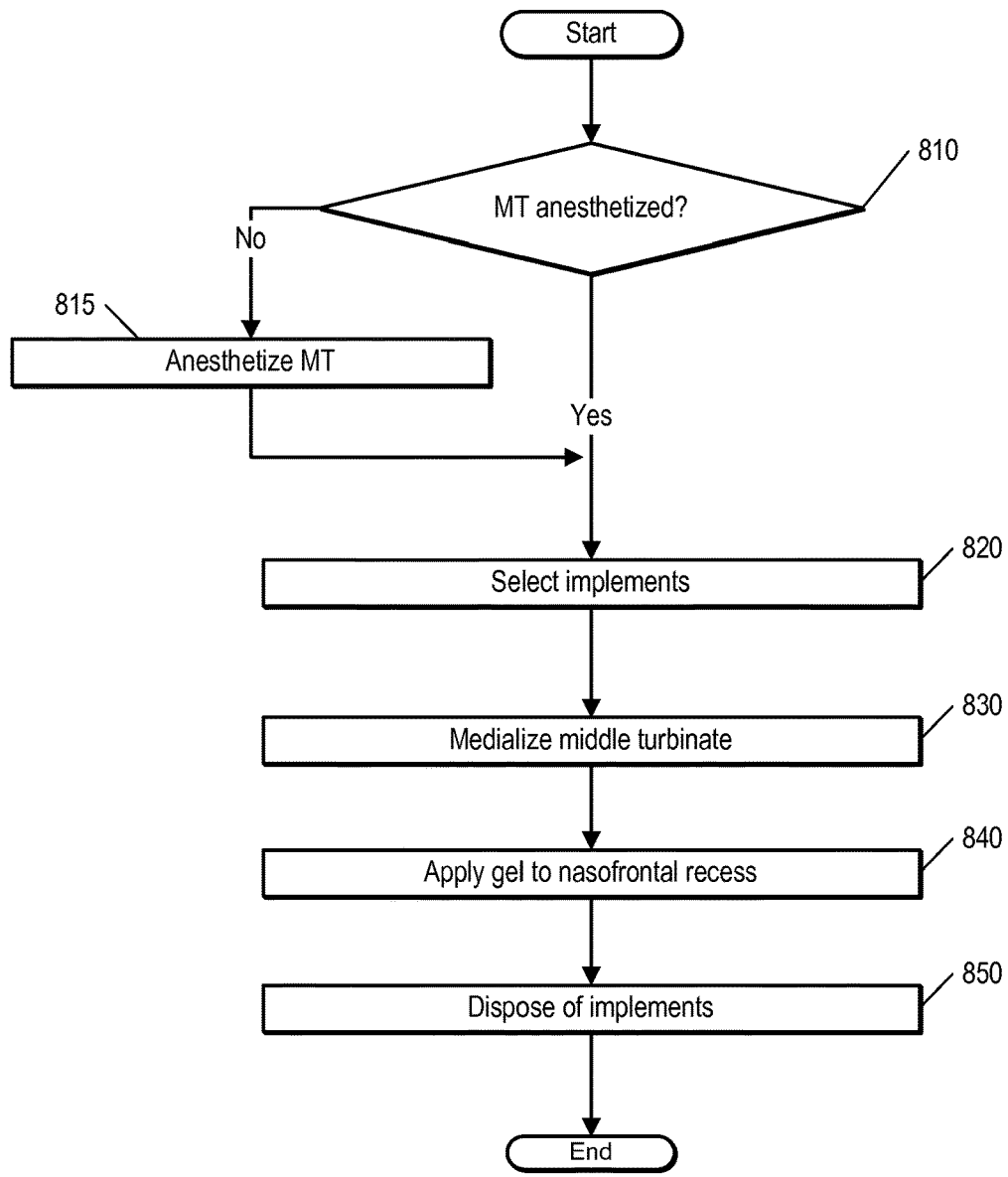
FIG. 8 is a flow diagram illustrating a method of treating the sinuses, according to one embodiment.

FIG. 8 is a flow diagram illustrating a method of treating the sinuses, according to one embodiment. Specifically, FIG. 8 illustrates elements of a procedure for anesthetizing a patient's nasofrontal recess prior to performing an in-office sinus procedure, such as balloon sinuplasty. FIG. 8 can be performed by a practitioner using a kit, such as kit 100 of FIG. 3.

At 810, the practitioner confirms whether the MT is effectively anesthetized. In one embodiment, the practitioner probes the area and questions the patient. If the patient discomfort is higher than expected, the practitioner provides additional anesthetic to the MT at 815. In one embodiment, this can be achieved by repacking the nose. Alternatively, the practitioner can spray additional topical anesthetic or can inject local anesthetic to the MT.

The practitioner selects, at 820, implements to anesthetize the nasofrontal recess (FR in FIG. 8). In one embodiment, all implements used for anesthetizing the FR are marked for identification as being associated with this portion of the procedure. In one embodiment, the practitioner selects an applicator, such as applicator 150 of FIG. 3. The practitioner also selects an anesthetic, such as an anesthetic gel 122 of FIG. 3, and a syringe, such as syringe 124 of FIG. 3. In one embodiment, the gel is a 4% tetracaine gel and the applicator is a 70 degree applicator. The physician mates the applicator e.g., using a threaded locking mechanism, to a 3cc syringe after loading the syringe with the anesthetic gel.

At 830, the practitioner medializes the middle turbinate (MT). Patient discomfort would prevent this operation, without performance of the preceding steps. Medializing the MT facilitates access to the sinuses. This fact and the location of the MT typically prevent access to higher portions of the OMU until after the anesthesia that results from the packing discussed with regard to FIG. 7. At 840, the practitioner applies an anesthetic agent to the nasofrontal recess. This enables performance of subsequent steps, such as the balloon sinuplasty procedure.

The practitioner disposes, at 850, of the implements used to anesthetize the FR. In one embodiment, disposing of the implements involves returning the implements to the locations in the kit from which the implements were previously removed. Alternatively, the implements can be placed in a waste receptacle, which can be included in the kit. Additional details are discussed with regard to FIG. 8A.

Figure 8A:
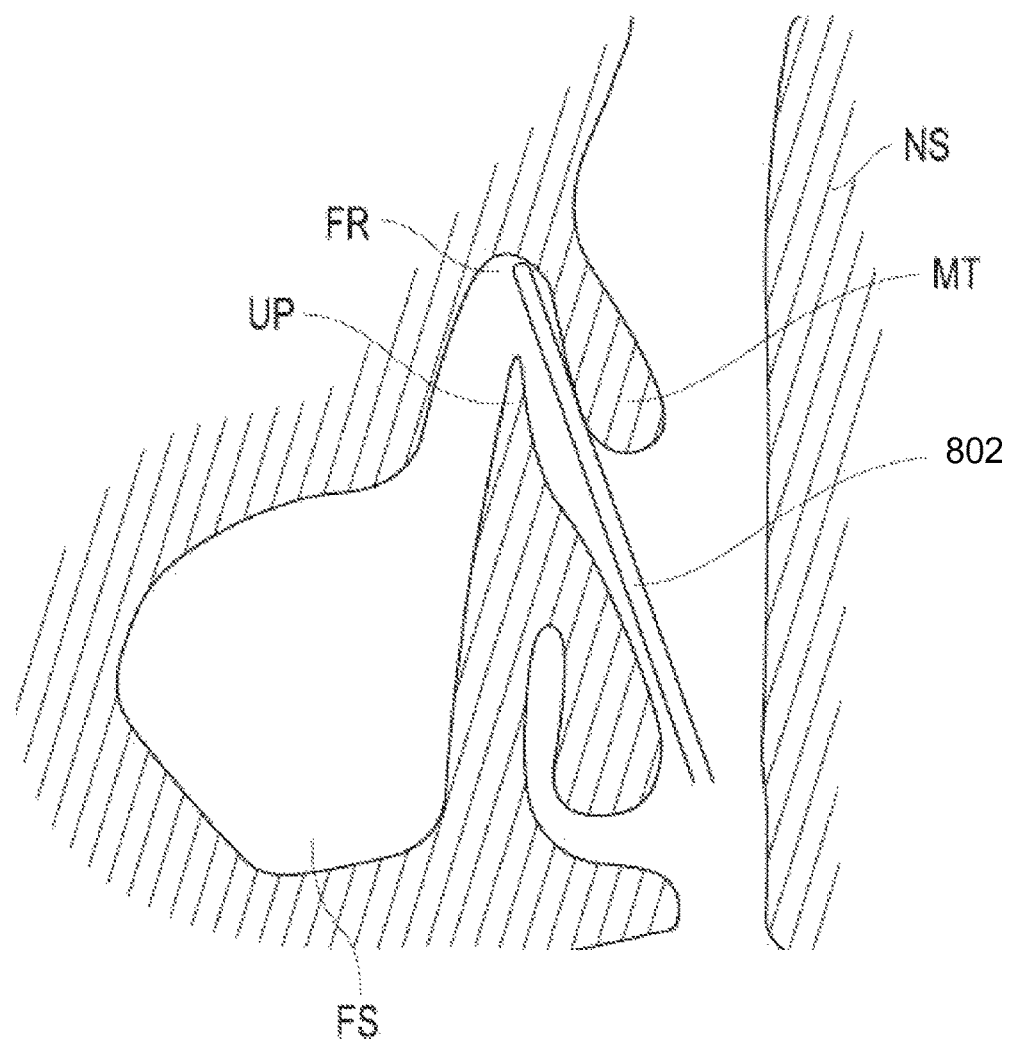
FIG. 8A is a coronal view of a portion of the sinuses being treated, according to one embodiment.

FIG. 8A is a coronal view of a portion of the sinuses being treated, according to one embodiment. An applicator 802 is shown inserted past the MT and into the FR. The applicator is configured with an axial lumen via which a topical anesthetic, e.g., the anesthetic gel, is dispensed. The anesthetic gel is introduced to the lumen at a proximal end, e.g., by pressure on a syringe mated to the applicator. The anesthetic gel, having traversed the lumen, is dispensed from the distal end of the applicator onto the surface of the lateral nasal wall.

Figure 9:
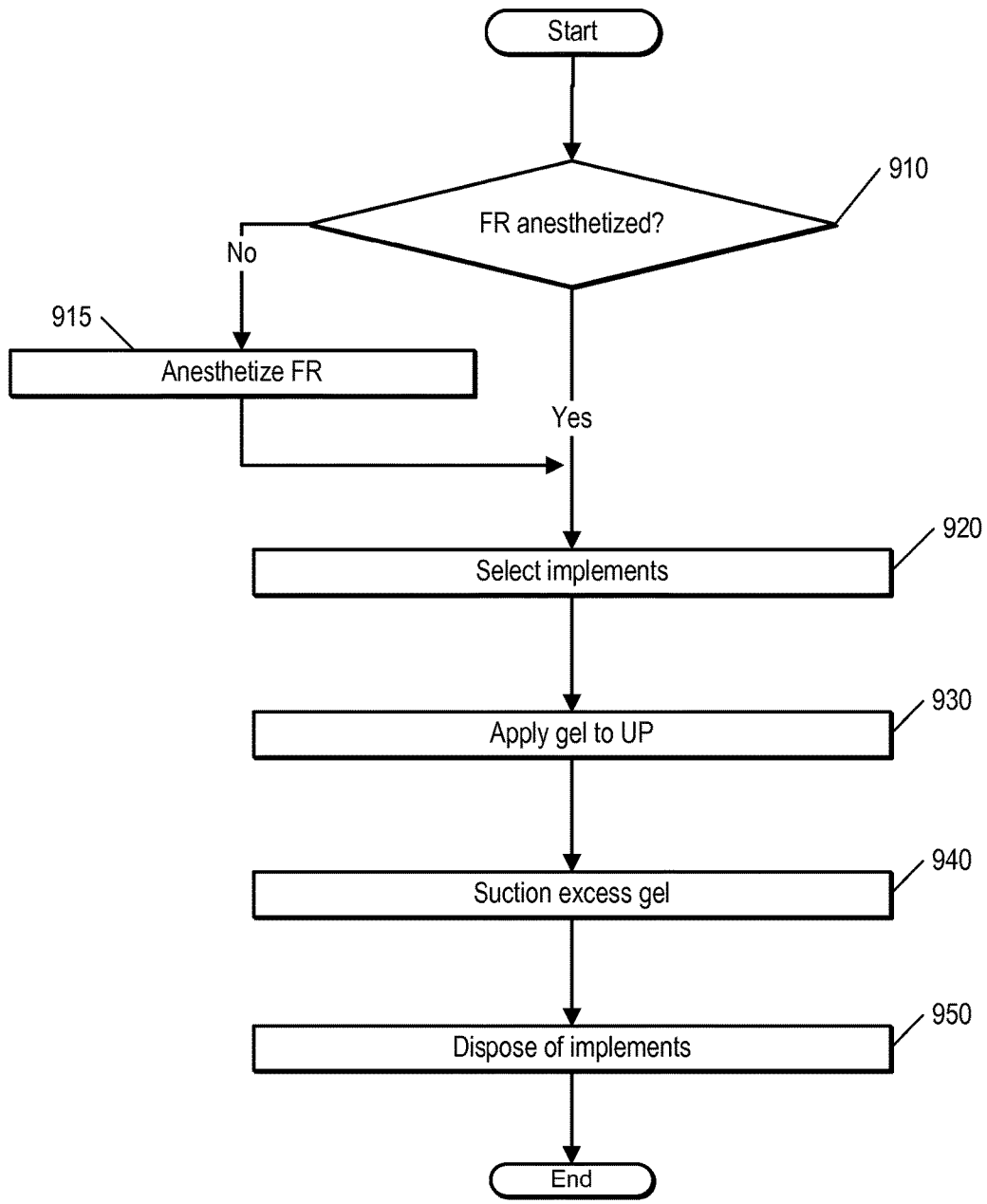
FIG. 9 is a flow diagram illustrating a method of treating the sinuses, according to one embodiment.

FIG. 9 is a flow diagram illustrating a method of treating the sinuses, according to one embodiment. Specifically, FIG. 9 illustrates elements of a procedure for anesthetizing a patient's UP and surfaces both lateral and medial to the UP prior to performing an in-office sinus procedure, such as balloon sinuplasty. FIG. 9 can be performed by a practitioner using a kit, such as kit 100 of FIG. 3.

At 910, the practitioner confirms whether the FR is effectively anesthetized. In one embodiment, the practitioner probes the area and questions the patient. If the patient discomfort is higher than expected, the practitioner provides additional anesthetic to the FR at 815. In one embodiment, this can be achieved by delivering additional anesthetic gel to the FR using the applicator as discussed with regard to FIG. 8.

The practitioner selects, at 920, implements to anesthetize the underside of the uncinate process (UP in FIG. 9). In one embodiment, all implements used for anesthetizing the UP are marked for identification as being associated with this portion of the procedure. In one embodiment, the practitioner selects an applicator, such as applicator 152 of FIG. 3. The practitioner also selects an anesthetic, such as an anesthetic gel 122 of FIG. 3, and a syringe, such as syringe 126 of FIG. 3. In one embodiment, the anesthetic gel is a 4% tetracaine gel and the applicator is a 110 degree applicator. The physician mates the applicator e.g., using a threaded locking mechanism, to a 3cc syringe after loading the syringe with the anesthetic gel.

At 930, the practitioner applies an anesthetic agent to the uncinate process (UP). In one embodiment, the practitioner applies the anesthetic agent to the lateral and medial surfaces of the UP, in addition to the underside of the UP. This enables performance of subsequent steps, such as the balloon sinuplasty procedure. In one embodiment, the practitioner also smears anesthetic gel on the face of the ethmoid. This provides additional anesthesia for the ethmoid sinuses and facilitates an ethmoidectomy, if indicated.

At 940, the practitioner removes excess anesthetic (if any). 940 can be performed after a delay, e.g., 3-4 minutes, to allow the anesthetic to take effect. Suctioning the anesthetic gel can be performed by the practitioner reversing the pull on the syringe mated to the applicator or using a device designed for suction purposes.

The practitioner disposes, at 950, of the implements used to anesthetize the UP. In one embodiment, disposing of the implements involves returning the implements to the locations in the kit from which the implements were previously removed. Alternatively, the implements can be placed in a waste receptacle, which can be included in the kit. Additional details are discussed with regard to FIG. 9A.

Figure 9A:
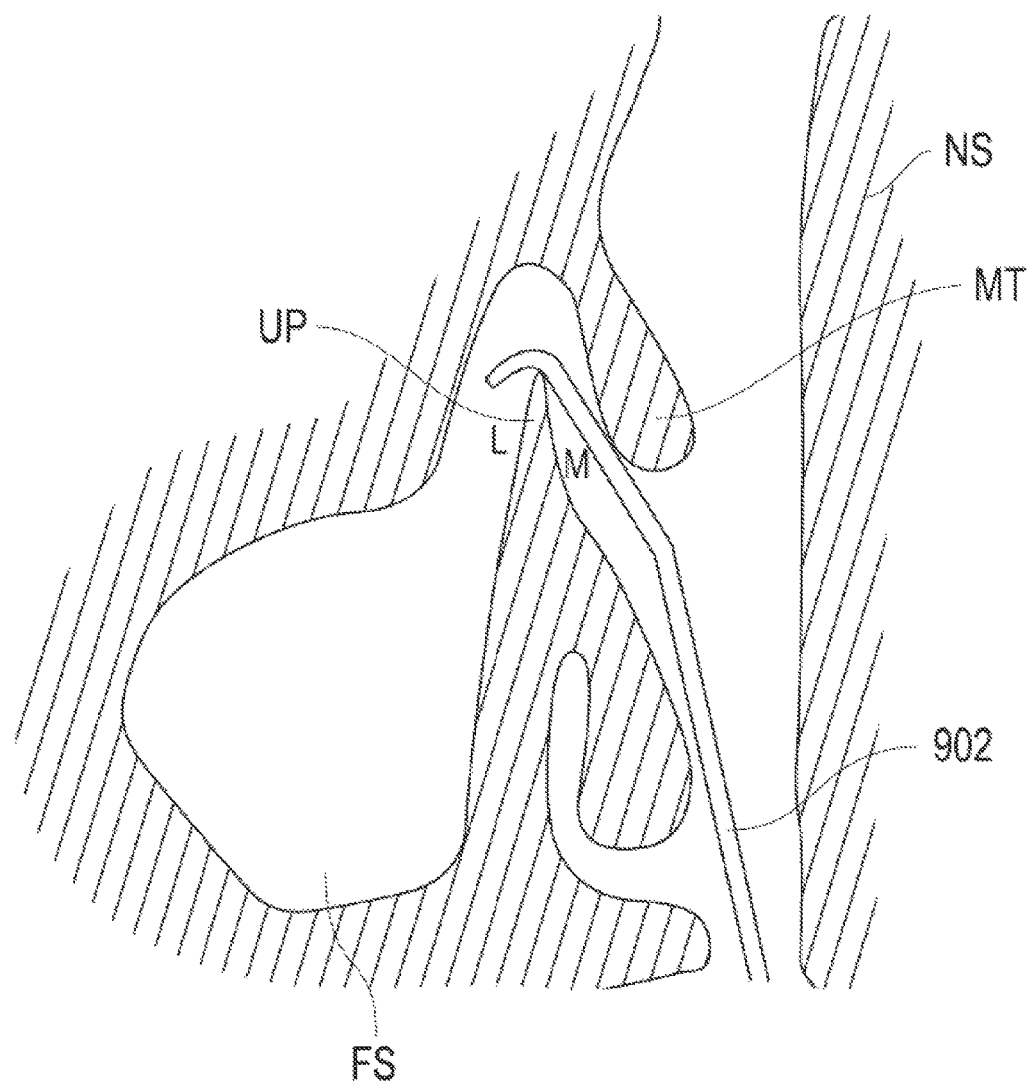
FIG. 9A is a coronal view of a portion of the sinuses being treated, according to one embodiment.

FIG. 9A is a coronal view of a portion of the sinuses being treated, according to one embodiment. An applicator 902 is shown inserted along the UP. The distal end of the applicator is inserted under the UP. The applicator is configured with an axial lumen via which a topical anesthetic, e.g., the anesthetic gel, is dispensed. The anesthetic gel is introduced to the lumen at a proximal end, e.g., by pressure on a syringe mated to the applicator. The anesthetic gel, having traversed the lumen, is dispensed from the distal end of the applicator. In one embodiment, the applicator is also positioned to deliver the anesthetic gel to the lateral and medial surfaces of the UP, as indicated by L and M, respectively, in FIG. 9A, in addition to the underside of the UP.

Figure 10:
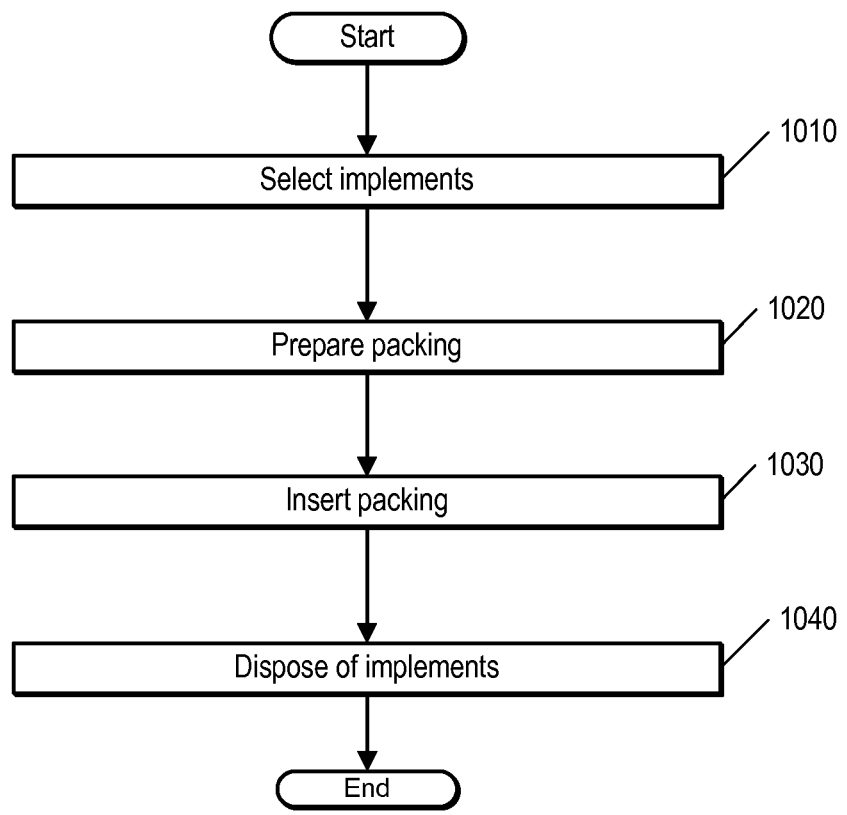
FIG. 10 is a flow diagram illustrating a method of treating the sinuses, according to one embodiment.

FIG. 10 is a flow diagram illustrating a method of treating the sinuses, according to one embodiment. Specifically, FIG. 10 illustrates elements of a procedure for anesthetizing a patient's sphenoid opening prior to performing an in-office sinus procedure, such as balloon sinuplasty. FIG. 10 can be performed by a practitioner using a kit, such as kit 100 of FIG. 3.

The practitioner selects, at 1010, implements used to anesthetize the sphenoid opening by introducing packing into the sphenoid opening. In one embodiment, all implements used for packing the sphenoid opening are marked for identification as being associated with this portion of the procedure. In one embodiment, the practitioner selects an emesis basin, such as 114 or 116 of FIG. 3. The practitioner also retrieves at least one cotton piece and/or cottonoids such as 134 of FIG. 3. The practitioner also retrieves a mixture of anesthetic and vasoconstrictor. In one embodiment, the mixture is a combination of a 4% tetracaine solution with epinephrine in a 1:3000) concentration. The mixture can be pre-mixed or can be mixed at the time of selection. Pre-mixing promotes use of a safe and effective concentration. To introduce the packing into the nose, the practitioner selects one or more implements, such as an ear curette (e.g., 154 of FIG. 3) and/or a toothless alligator (e.g., 138 of FIG. 3).

At 1020, the practitioner prepares the packing. In one embodiment, this involves the practitioner placing the packing into the emesis basin and soaking the packing with the mixture. Once the packing is saturated, or the desired amount of the mixture is absorbed, the practitioner can compress the packing to remove excess fluid.

The practitioner introduces the packing into the nasal passage near the nasal septum and sphenoethmoidal recess at 1030. The packing is inserted using toothless alligators and/or an ear curette. The shape and conformability of the packing ensure that the entire surfaces of the MT and nearby structures are safely and effectively anesthetized. Using conformable structures containing anesthetic and/or vasoconstrictive agents, the practitioner anesthetizes further into the nasal passages, allowing performance of subsequent steps. Additional details regarding the anesthetic packing are discussed with regard to FIG. 10A. The packing is left in place for a period of time, such as ten minutes. Then the physician removes the packing.

The practitioner disposes, at 1040, of the implements used to pack OMU. In one embodiment, disposing of the implements involves returning the implements to the locations in the kit from which the implements were previously removed. Alternatively, the implements can be placed in a waste receptacle, which can be included in the kit.

Figure 10A:
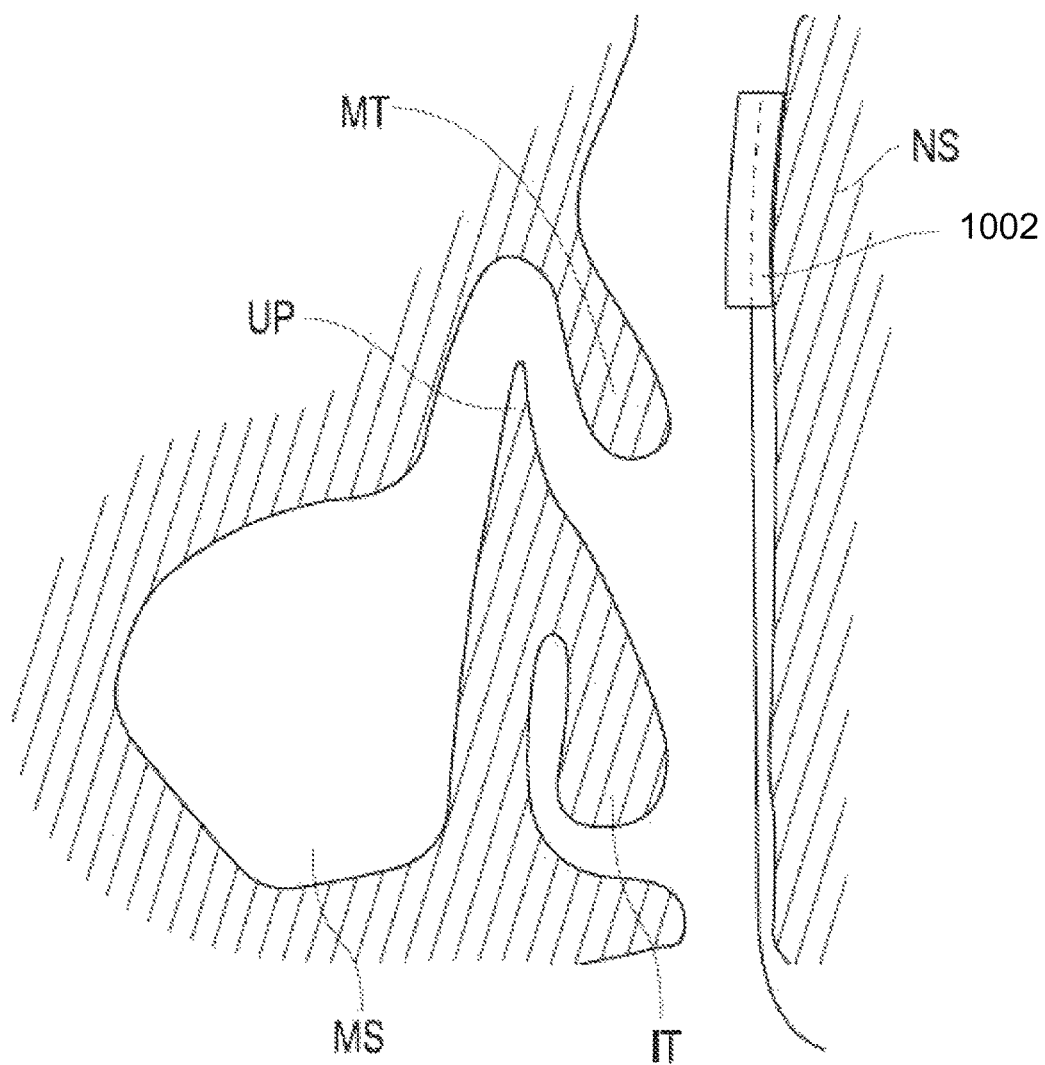
FIG. 10A is a coronal view of a portion of the sinuses being treated, according to one embodiment.

FIG. 10A is a coronal view of a portion of the sinuses being treated, according to one embodiment. In some cases, the physician will anesthetize additional nasal structures to enable access to the sphenoid sinuses. The physician places cottoniod 1002 between the nasal septum and the middle turbinate as posteriorly as possible. The physician then lateralizes the MT. The physician smears anesthetic gel on the sphenoid surface. The physician can use a sphenoid seeker to locate the sphenoid opening.

Figure 11:
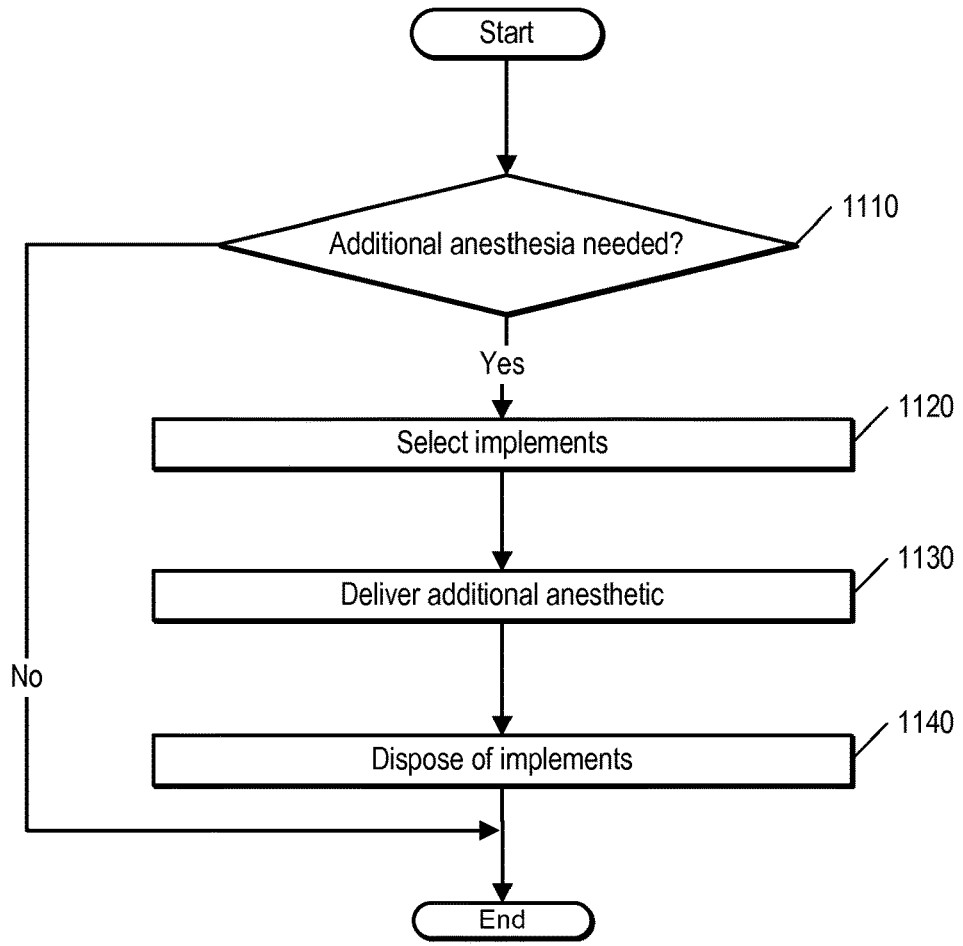
FIG. 11 is a flow diagram illustrating a method of treating the sinuses, according to one embodiment.

FIG. 11 is a flow diagram illustrating a method of treating the sinuses, according to one embodiment. FIG. 11 can be performed by a practitioner using a kit, such as kit 100 of FIG. 3.

At 1110, the practitioner determines whether additional anesthesia is needed. In one embodiment, the practitioner probes the nasal structures of the patient and queries the patient to determine if additional anesthetic should be applied. If so, e.g., if the practitioner determines that the patient will likely have discomfort tolerating a subsequent procedure, such as balloon sinuplasty, the practitioner selects, at 1120, implements used to deliver additional anesthetic. In one embodiment, all implements used for delivering additional anesthetic are marked for identification as being associated with this portion of the procedure. Alternatively, the practitioner can select implement previously used in other portions of the procedure. In one embodiment, the practitioner selects a needle, such as needle 132 of FIG. 3. The practitioner also selects a syringe, such as syringe 130 of FIG. 3 and an anesthetic, such as anesthetic 121 of FIG. 3. The practitioner mates the needle e.g., using a threaded locking mechanism, to the syringe after loading the syringe with the anesthetic.

In some cases, at 1130, the practitioner injects anesthetic. The practitioner disposes, at 1140, of the implements used to achieve additional anesthesia. In one embodiment, disposing of the implements involves returning the implements to the locations in the kit from which the implements were previously removed. Alternatively, the implements can be placed in a waste receptacle, which can be included in the kit. Once the additional anesthesia is performed, the physician can perform the balloon sinuplasty procedure safely and without undue discomfort for the patient.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. A kit for facilitating performance of a surgical procedure, comprising:
    a first container, containing a first agent, wherein
        the surgical procedure is a sinus procedure comprising at least one of
            a functional endoscopic sinus surgery procedure, or
            a balloon sinuplasty procedure, and
        the first agent is configured to modulate a rate of absorption of a subsequently-applied topical agent by one or more nasal structures;
    a first applicator configured to apply the first agent to a first portion of the one or more nasal structures, as part of a first portion of the surgical procedure;
    a second container, containing a second agent, wherein
        the second agent is configured to anesthetize the first portion of the one or more nasal structures, subsequent to application of the first agent; and
    a second applicator configured to apply the second agent to the first portion of the one or more nasal structures, as part of a second portion of the surgical procedure;
    a sphenoid seeker, wherein
        the one or more nasal structures comprise a sphenoid sinus, and
        the sphenoid seeker, by facilitating location of a sphenoid opening, is adapted to facilitate, as part of the surgical procedure,
            application of the first agent to the sphenoid sinus, using the first applicator, and
            application of the second agent to the sphenoid sinus, using the second applicator; and
    a tray, wherein
        the tray comprises a plurality of recesses in an interior surface thereof,
        the plurality of recesses comprises one or more recesses,
        a first recess of the plurality of recesses is configured to secure the first applicator,
        a second recess of the plurality of recesses is configured to secure the second applicator,
        a third recess of the plurality of recesses is configured to secure the sphenoid seeker,
        the tray is configured to secure the first container in a first one of the one or more recesses,
        the tray is configured to secure the second container in a second one of the one or more recesses,
        the one or more recesses are other than the first recess and the second recess,
        the first recess, the second recess, and the one or more recesses are arranged in the tray such that
            the first agent and the first applicator are associated with one another by virtue of the first recess and the first one of the one or more recesses being located in proximity to one another, and
            the second agent and the second applicator are associated with one another by virtue of the second recess and the second one of the one or more recesses being located in proximity to one another.

2. The kit of claim 1, further comprising:
    a third container, wherein
        the third container contains a third agent configured to anesthetize a second portion of the one or more nasal structures, subsequent to application of the second agent, and the tray is configured to secure the third container in a third one of one or more recesses of the plurality of recesses; and
a third applicator configured to apply the third agent to the second portion of the one or more nasal structures, as part of a third portion of the surgical procedure, wherein
a third recess of the plurality of recesses is configured to secure the third applicator, and
the third agent and the third applicator are associated with one another by virtue of a third recess and a third one of the one or more recesses being located in proximity to one another and being identified as associated with one another by marking information affixed to the tray.

3. The kit of claim 1, further comprising:
a long tipped atomizer, wherein
the long tipped atomizer is adapted to spray a third agent into one or more nasal passages of the one or more nasal structures,
the plurality of recesses comprises a third recess,
the third recess of the plurality of recesses is configured to secure the long tipped atomizer,
the second applicator comprises a first plurality of conformable structures,
the second applicator comprises a second plurality of retrievable structures, and
the second recess of the plurality of recesses is configured to secure
the first plurality of conformable structures of the second applicator, and
the second plurality of retrievable structures of the second applicator.

4. The kit of claim 3, wherein
the long tipped atomizer comprises an elongate member comprising
a proximal end,
a distal end, and
an axial lumen,
the distal end being adapted to access a naso-frontal recess by virtue of the long tipped atomizer being flexible, and
the long tipped atomizer is adapted to deliver the third agent to the naso-frontal recess via the axial lumen.

5. The kit of claim 1, further comprising:
a combination freer elevator and sphenoid seeker, wherein
the sphenoid seeker is comprised in the combination freer elevator and sphenoid seeker,
the combination freer elevator and sphenoid seeker further comprises a freer elevator,
the third recess of the plurality of recesses is adapted to secure the combination freer elevator and sphenoid seeker,
the freer elevator of the combination freer elevator and sphenoid seeker is adapted for use in positioning a middle turbinate; and
a removable cover, wherein
the first container, the first applicator, the second container, the second applicator, and the combination freer elevator and sphenoid seeker are sealed within the tray by virtue of the removable cover being attached to the tray,
the first agent comprises a composition of a first anesthetic and a first vasoconstrictive agent, and
the composition is mixed according to a formula that is anesthetically effective in the sinus procedure, prior to the tray being sealed by the removable cover.

6. The kit of claim 1, further comprising:
a third container, wherein
the tray is configured to secure the third container in a third one of the one or more recesses of the plurality of recesses,
the third container contains a third agent,
the first agent is a first vasoconstrictive agent,
the second agent is an anesthetic agent,
the third agent is a second vasoconstrictive agent,
the anesthetic agent and the second vasoconstrictive agent are associated with one another by virtue of the second one of the one or more recesses and the third one of the one or more recesses being located in proximity to one another.

7. The kit of claim 1, wherein the tray further comprises:
marking information, wherein
the marking information is affixed to the tray and comprises
associating information affixed to the tray, wherein
the first agent and the first applicator are further associated with one another by the associating information, and
the second agent and the second applicator are further associated with one another by the associating information, and
sequence information affixed to the tray, wherein
the sequence information indicates that
the first agent and the first applicator are to be used in the first portion of the surgical procedure, and
the second agent and the second applicator are to be used in the second portion of the surgical procedure.

8. The kit of claim 7, wherein
the marking information indicates an anatomical structure of a patient, and
the anatomical structure is at least one of
a sinus structure, or
a nasal structure.

9. The kit of claim 1, further comprising:
a maxillary seeker, wherein
the sinus procedure is the balloon sinuplasty procedure,
the maxillary seeker is adapted to facilitate insertion of a balloon into a sinus by introducing a space between an uncinate and lateral nasal wall, and
a fourth recess of the plurality of recesses is configured to secure the maxillary seeker.

10. A method for using a kit in a surgical procedure, comprising:
retrieving a first container from a tray of the kit, wherein
the surgical procedure is a sinus procedure, performed on one or more nasal structures and comprising at least one of
a functional endoscopic sinus surgery procedure, or
a balloon sinuplasty procedure, and
the first container contains a first agent,
the tray comprises a plurality of recesses in an interior surface thereof,
the plurality of recesses comprises one or more recesses,
the tray is configured to secure the first container in a first one of the one or more recesses, and
the first container is retrieved from the first one of the one or more recesses;
retrieving a first applicator from the tray, wherein
the first applicator is retrieved from a first recess of the plurality of recesses, the first recess is configured to secure the first applicator in the tray, and
the first applicator is configured to apply the first agent;
retrieving a sphenoid seeker from the tray, wherein
the sphenoid seeker is retrieved from a second recess of the plurality of recesses,
the one or more nasal structures comprise a sphenoid sinus, and
the sphenoid seeker, by facilitating location of a sphenoid opening, is adapted to facilitate, as part of the surgical procedure,
application of the first agent to the sphenoid sinus, using the first applicator, and
application of a second agent to the sphenoid sinus, using a second applicator; and
as part of a first portion of the surgical procedure, using the sphenoid seeker and first applicator to apply the first agent to a first portion of the sphenoid sinus, wherein
the first agent is configured to modulate a rate of absorption of a subsequently-applied topical agent by the sphenoid sinus;
retrieving a second container from the tray, wherein
the second container contains the second agent,
the tray is configured to secure the second container in a second one of one or more recesses of the plurality of recesses, and
the second container is retrieved from the second one of the one or more recesses;
retrieving the second applicator from the tray, wherein
the second applicator is retrieved from a second recess of the plurality of recesses,
the second recess is configured to secure the second applicator in the tray,
the second applicator is configured to apply the second agent, and
the one or more recesses are other than the first recess and the second recess; and
as part of a second portion of the surgical procedure, using the sphenoid seeker and
second applicator to apply the second agent to the first portion of the sphenoid
sinus, subsequent to the applying the first agent, wherein
the second agent is configured to anesthetize the first portion of the sphenoid sinus, and
the first recess, the second recess, and the one or more recesses are arranged in the tray such that
the first agent and the first applicator are associated with one another by virtue of the first recess and the first one of the one or more recesses being located in proximity to one another, and
the second agent and the second applicator are associated with one another by virtue of the second recess and the second one of the one or more recesses being located in proximity to one another.

11. The method of claim 10, further comprising
retrieving a third container from the tray, wherein
the third container contains a third agent,
the tray is configured to secure the third container in a third one of one or more recesses of the plurality of recesses, and
the third container is retrieved from the third one of the one or more recesses;
retrieving a long tipped atomizer from the tray, wherein
the long tipped atomizer is retrieved from a third recess of the plurality of recesses,
the third recess is configured to secure the long tipped atomizer in the tray, and
the long tipped atomizer is configured to apply the third agent; and
as part of a third portion of the surgical procedure, using the long tipped atomizer to apply the third agent to one or more nasal passages,
subsequent to the second agent being applied, wherein
the third agent and the long tipped atomizer are associated with one another by virtue of a third recess and a third one of the one or more recesses being located in proximity to one another and being identified as associated with one another by marking information affixed to the tray.

12. The method of claim 11, wherein
the first agent is a vasoconstrictive agent,
the third agent is an anesthetic agent,
the vasoconstrictive agent and the anesthetic agent are associated with one another by virtue of the first one of the one or more recesses and the third one of the one or more recesses being located in proximity to one another, and
the second recess of the plurality of recesses is configured to secure
a first plurality of conformable structures of the second applicator, and
a second plurality of retrievable structures of the second applicator.

13. The method of claim 11, wherein
the long tipped atomizer comprises an elongate member comprising
a proximal end,
a distal end, and
an axial lumen,
the distal end being adapted to access a naso-frontal recess by virtue of the long tipped atomizer being flexible, and
the long tipped atomizer is adapted to deliver the third agent to the naso-frontal recess via the axial lumen.

14. The method of claim 10, further comprising:
retrieving a combination freer elevator and sphenoid seeker from the tray, wherein
the sphenoid seeker is comprised in the combination freer elevator and sphenoid seeker,
the combination freer elevator and sphenoid seeker further comprises a freer elevator,
the retrieving the sphenoid seeker from the tray is comprised in the retrieving the combination freer elevator and sphenoid seeker,
the second recess of the plurality of recesses is adapted to secure the combination freer elevator and sphenoid seeker,
the first container, the first applicator, the second container, the second applicator, and the combination freer elevator and sphenoid seeker are sealed within the tray by virtue of a removable cover being attached to the tray,
the first agent comprises a composition of a first anesthetic and a first vasoconstrictive agent, and
the composition is mixed according to a formula that is anesthetically effective in the sinus procedure, prior to the tray being sealed by the removable cover; and
as part of the second portion of the surgical procedure, positioning a middle turbinate using the freer elevator of the combination freer elevator and sphenoid seeker.

15. The method of claim 10, further comprising:
as part of a fourth portion of the surgical procedure, retrieving a maxillary seeker,
wherein
the sinus procedure is the balloon sinuplasty procedure,
the maxillary seeker is adapted to facilitate insertion of a balloon into a sinus by introducing a space between an uncinate and lateral nasal wall, and
a fourth recess of the plurality of recesses is configured to secure the maxillary seeker;
introducing a space between an uncinate of the one or more nasal structures and lateral nasal wall of the one or more nasal structures, using the maxillary seeker; and
inserting a balloon into a sinus of the one or more nasal structures through the space.

16. An apparatus for facilitating performance of a surgical procedure, comprising:
a first containing means for containing a first agent, wherein
the surgical procedure is a sinus procedure comprising at least one of
a functional endoscopic sinus surgery procedure, or
a balloon sinuplasty procedure, and
the first agent is configured to modulate a rate of absorption of a subsequently-applied topical agent by one or more nasal structures, as part of a first portion of the surgical procedure;
a first applying means for applying the first agent to a first portion of the one or more nasal structures;
a second containing means for containing a second agent, wherein
the second agent is configured to anesthetize the first portion of the one or more nasal structure; and
a second applying means for applying the second agent to the first portion of the one or more nasal structures, subsequent to application of the first agent, wherein
the apparatus comprises a plurality of recesses in an interior surface of a tray thereof,
a first recess of the plurality of recesses is configured to secure the first applying means,
a second recess of the plurality of recesses is configured to secure the second applying means,
the tray is configured to secure the first containing means in a first one of one or more recesses of the plurality of recesses,
the tray is configured to secure the second containing means in a second one of the one or more recesses of the plurality of recesses,
the one or more recesses are other than the first recess and the second recess, and
the first recess, the second recess, and the one or more recesses are arranged in the tray such that
the first agent and the first applying means are associated with one another by virtue of the first recess and the first one of the one or more recesses being located in proximity to one another, and
the second agent and the second applying means are associated with one another by virtue of the second recess and the second one of the one or more recesses being located in proximity to one another; and
a sphenoid locating means for facilitating location of a sphenoid opening, wherein
a third recess of the plurality of recesses is configured to secure the sphenoid seeker,
the one or more nasal structures comprise a sphenoid sinus, and
the sphenoid locating means is adapted to facilitate, as part of the surgical procedure,
application of the first agent to the sphenoid sinus, using the first applying means, and
application of the second agent to the sphenoid sinus, using the second applying means.

17. The apparatus of claim 16, further comprising:
a third containing means for containing a third agent configured to anesthetize a second portion of the one or more nasal structures, subsequent to application of the second agent, wherein
the tray is configured to secure the third containing means in a third one of one or more recesses of the plurality of recesses; and
a third applying means for applying the third agent to a second portion of the one or more nasal structures, subsequent to application of the second agent, wherein
the third applying means is adapted to spray a third agent into one or more nasal passages of the one or more nasal structures, and
the third agent and the third applying means are associated with one another by virtue of a third recess and a third one of the one or more recesses being located in proximity to one another and being identified as associated with one another by marking information affixed to the tray.

18. The apparatus of claim 17, wherein
the first agent is a vasoconstrictive agent,
the third agent is an anesthetic agent, and
the vasoconstrictive agent and the anesthetic agent are associated with one another by virtue of the first one of the one or more recesses and the third one of the one or more recesses being located in proximity to one another and
the second recess of the plurality of recesses is configured to secure
a first plurality of conformable structures of the second applicator, and
a second plurality of retrievable structures of the second applicator.

19. The apparatus of claim 17, wherein
the third applying means comprises an elongate member comprising
a proximal end,
a distal end, and
an axial lumen,
the distal end being adapted to access a naso-frontal recess by virtue of the third applying means being flexible, and
the third applying means is adapted to deliver the third agent to the naso-frontal recess via the axial lumen.

20. The apparatus of claim 16, further comprising:
an introducing means for introducing a space between an uncinate and lateral nasal wall,
wherein
the sinus procedure is the balloon sinuplasty procedure,
the introducing means facilitates insertion of a balloon into a sinus, and
a fourth recess of the plurality of recesses is configured to secure the introducing means.

21. The kit of claim 1, further comprising:
a third container, wherein
the tray is configured to secure the third container in a third one of the one or more recesses of the plurality of recesses, the third container contains a third agent,
the first agent is a vasoconstrictive agent,
the third agent is an anesthetic agent, and
the vasoconstrictive agent and the anesthetic agent are associated with one another by virtue of the first one of the one or more recesses and the third one of the one or more recesses being located in proximity to one another.

22. The kit of claim 21, wherein
the first container contains a first amount of the vasoconstrictive agent,
the third container contains a second amount of the anesthetic agent, and
the first amount and the second amount are such that, upon the first container and the third container being retrieved from the kit, and the first amount of the vasoconstrictive agent and the second amount of the anesthetic agent being mixed, a mixture in a ratio according to a formula that is anesthetically effective in the sinus procedure is produced.

23. The kit of claim 21, wherein the tray further comprises:
marking information, wherein
the marking information is affixed to the tray and comprises
associating information affixed to the tray, wherein
the vasoconstrictive agent and the anesthetic agent are further associated with one another by the associating information, and
sequence information affixed to the tray, wherein
the sequence information indicates that the vasoconstrictive agent and the anesthetic agent are to be used in the first portion of the sinus procedure.

24. The kit of claim 6, wherein
the second container contains a first amount of the anesthetic agent,
the third container contains a second amount of the second vasoconstrictive agent, and
the first amount and the second amount are such that, upon the second container and the third container being retrieved from the kit, and the first amount of the anesthetic agent and the second amount of the second vasoconstrictive agent being mixed, a mixture in a ratio according to a formula that is anesthetically effective in the sinus procedure is produced.

25. The method of claim 12, wherein
the first container contains a first amount of the vasoconstrictive agent,
the third container contains a second amount of the anesthetic agent, and
the first amount and the second amount are such that, upon the first container and the third container being retrieved from the kit, and the first amount of the vasoconstrictive agent and the second amount of the anesthetic agent being mixed, a mixture in a ratio according to a formula that is anesthetically effective in the sinus procedure is produced.

* * * * *